United States Patent [19]
Fodgaard et al.

[11] Patent Number: 5,817,007
[45] Date of Patent: Oct. 6, 1998

[54] METHOD AND AN APPARATUS FOR DETERMINING THE CONTENT OF A CONSTITUENT OF BLOOD OF AN INDIVIDUAL

[75] Inventors: Henrik Fodgaard, Copenhagen; Rolf Singer, Fredensborg; Paul Erik Fabricius, Struer, all of Denmark

[73] Assignee: Bang & Olufsen Technology A/S, Denmark

[21] Appl. No.: 591,663

[22] PCT Filed: Aug. 1, 1994

[86] PCT No.: PCT/DK94/00297

§ 371 Date: Apr. 26, 1996

§ 102(e) Date: Apr. 26, 1996

[87] PCT Pub. No.: WO95/04266

PCT Pub. Date: Feb. 9, 1995

[30] Foreign Application Priority Data

Jul. 30, 1993 [DK] Denmark ............... 0888/93

[51] Int. Cl.⁶ .................................................. A61B 5/00
[52] U.S. Cl. ........................ 600/322; 600/473; 356/39
[58] Field of Search ............................... 128/633, 634, 128/664; 356/39–41; 600/310, 311, 314, 315, 316, 317, 322, 323, 324, 325, 326, 473

[56] References Cited

U.S. PATENT DOCUMENTS

| | | | |
|---|---|---|---|
| 4,134,678 | 1/1979 | Brown et al. ............... | 356/39 |
| 4,444,498 | 4/1984 | Heinemann ............... | 128/633 |
| 4,745,279 | 5/1988 | Karkar et al. ............... | 356/40 |
| 5,351,686 | 10/1994 | Steuer et al. ............... | 128/633 |
| 5,361,758 | 11/1994 | Hall et al. ............... | 128/633 |

FOREIGN PATENT DOCUMENTS 0 419 223  3/1991  European Pat. Off. .

OTHER PUBLICATIONS

Haaland, D.M. et al "Partial Least–Squares Methods for Spectral Analyses. etc.", Anal. Chem. 60:1193–1202 (1988).
Haaland, D.M. et al, "Partial Least–Squares Methods for Spectral Analyses. etc.", Anal. Chem. 60:1202–1208 (1988).
Geladi, P. et al, "Partial Least–Squares Regression: A Tutorial", Anal. Chimica Acta 185:1–17 (1986).
Webster, J.G., "Encyclopedia of Medical Devices and Instrumentation", vol. 3: 1695–1711 (1988).

*Primary Examiner*—Jennifer Bahr
*Assistant Examiner*—Eric F. Winakur
*Attorney, Agent, or Firm*—Bryan Cave LLP

[57] ABSTRACT

A method and an apparatus for determining the content of a constituent of blood of an individual are disclosed. In the method a whole blood stream is extracted from a blood vessel of said individual, the stream being directed through a path defining a substantially non-varying flow-through area wherein is provided a flow-through measuring cuvette including opposite first and second optical transparent surface parts defining an optical transmission path of the order of 0.5–2.0 mm. The whole blood stream flowing through the measuring cuvette is irradiated by irradiating the first optical transparent surface part of the measuring cuvette with multi-wavelength near infrared light. The near infrared absorption spectrum is detected and the content of the constituent is quantified on the basis of the detected near infrared absorption data. The method is particularly suited for measuring constituents of whole blood in an extracorporeal loop, for example in hemodialysis.

22 Claims, 11 Drawing Sheets

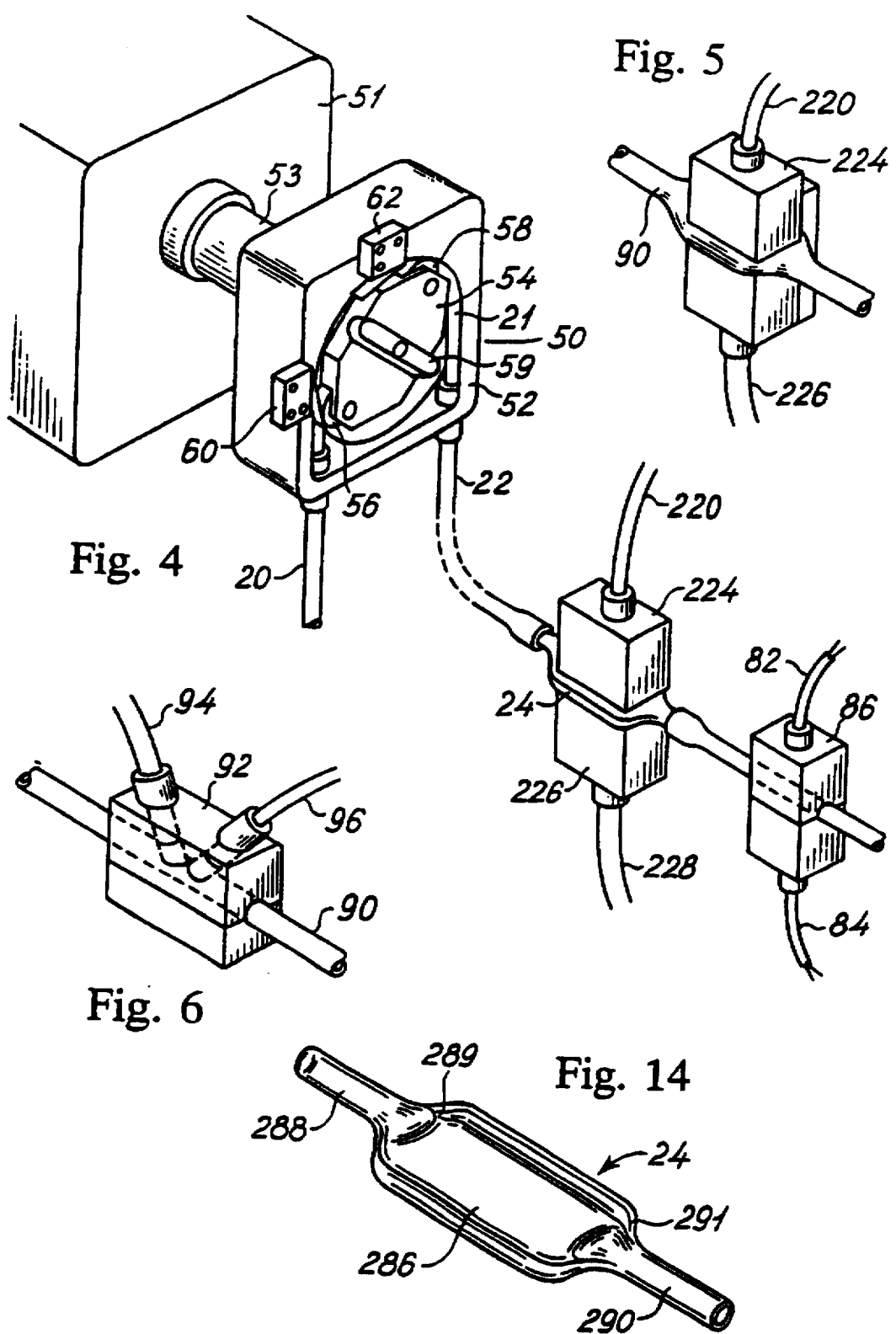

METHOD AND AN APPARATUS FOR DETERMINING THE CONTENT OF A CONSTITUENT OF BLOOD OF AN INDIVIDUAL

The present invention relates to novel techniques of determining the content of a constituent of blood of an individual and in particular a novel technique of determining the content of a constituent of blood of a hemodialysis patient.

Individuals suffering from kidney malfunction are treated by dialysis. By the conventional dialysis method, the blood of the patient in question is rinsed by means of a dialysis machine as the blood is contacted with a liquid known as the dialysate through a permeable membrane causing constituents of the blood to permeate through the membrane and be absorbed by substances of the dialysate. Reference is made to "Encyclopedia of Medical Devices and Instrumentation", vol. 3 16 95–1711 (1988) (Reference 4) in which a detailed discussion of the dialysis technique is presented.

In accordance with the conventional dialysis technique, the patient has his or her blood rinsed for a predetermined period of time which period of time is determined solely an empirical basis. Prior to the dialysis treatment, a blood sample may be collected from the patient which blood sample is analysed and similarly, a blood sample may be collected from the patient after the dialysis treatment has been finished. Through comparison of the two blood samples, the result of or the outcome of the dialysis treatment may be evaluated.

In numerous other situations such as during thorax surgery, a similar situation exists when blood is circulated extracorporeally through a heart-lung machine in order to replace or assist, for a limited time period, the heart or lung function.

An object of the present invention is to provide a novel technique rendering it possible to carry out a real-time or a quasi real-time analysis or determination of the content of a constituent of blood of an individual having his or her blood rinsed in a dialysis machine.

A further object of the present invention is to provide a novel technique rendering it possible to perform a real-time or a quasi real-time analysis or determination of the content of a constituent of blood of a patient when exposed to surgery or similarly having a whole blood stream of the order of 50–1,000 ml/min extracted from a blood vessel.

A feature of the present invention relates to the fact that the novel technique according to the present invention renders it possible to perform a multiconstituent analysis of blood of an individual in real-time or quasi real-time and further to compensate for any fluctuations of the blood flow of the blood stream.

A particular advantage of the present invention relates to the fact that in accordance with the teachings of the present invention, the dialysis treatment of a patient may be monitored in real-time or quasi real-time as a continuous determination or analysis of the constituent of blood such an the content of urea or any other relevant constituent may be determined in real-time or quasi real-time.

The above objects, the above feature and the above advantage together with numerous other objects, features and advantages which will be evident from the below description are in a first aspect of the invention obtained by a method of determining the content of a constituent of blood of an individual, comprising:

extracting a whole blood stream of the order of 50–1,000 ml/min from a blood vessel of said individual, directing said whole blood stream through a flow path defining a substantially non-varying flow-through area and comprising a flow-through measuring cuvette constituting part of said flow path, said flow-through measuring cuvette including opposite first and second optically transparent surface defining an optical transmission path of the order of 0.5–2.0 mm, irradiating said first optically transparent surface part of said flow-through measuring cuvette with multi-wavelength near infrared light so as to expose said whole blood stream flowing through said flow-through measuring cuvette to said multi-wavelength near infrared light, detecting the near infrared absorption spectrum represented by near infrared absorption data of said whole blood stream flowing through said flow-through measuring cuvette, and quantifying said content of said constituent by inputting said near infrared absorption data into a mathematical model representing the relation between the near infrared absorption data and the content of said constituent.

The above objects, the above feature and the above advantage together with numerous other objects, features and advantages are in a second aspect of the invention obtained by a method of determining the content of a constituent of blood of an individual, comprising:

extracting a whole blood stream of said individual from a blood vessel of said individual, directing said whole blood stream through a flow path comprising a flow-through measuring cuvette constituting part of said flow path, said flow-through measuring cuvette including at least one, optically transparent surface part, propelling said whole blood stream through said flow path by means of a pump causing said whole blood stream to flow through said flow path in a pulsed mode, monitoring said flow of said whole blood stream through said flow-through measuring cuvette of said flow path, so as to determine periods of substantially constant flow of said whole blood stream through said flow-through measuring cuvette, irradiating said at least one optically transparent surface part of said flow-through measuring cuvette with electromagnetic radiation of a specific spectral composition, so as to expose said whole blood stream flowing through said flow-through measuring cuvette to said electromagnetic radiation, detecting the electromagnetic radiation absorption spectrum, represented by electromagnetic radiation absorption data, of said whole blood stream flowing through said flow-through measuring cuvette at said periods of substantially constant flow of said whole blood stream flowing through said flow-through measuring cuvette, and quantifying said content of said constituent by inputting said electromagnetic radiation absorption data into a mathematical model representing the relation between electromagnetic radiation absorption data and the content of said constituent.

The above objects, the above feature and the above advantage together with numerous other objects, features and advantages which will be evident from the below description are in a third aspect of the invention obtained by an apparatus for determining the content of a constituent of blood of an individual, comprising:

means for extracting a whole blood stream from a blood vessel of said individual, a flow path defining a substantially non-varying flow-through area, means for directing said whole blood stream through said flow path, a flow-through measuring cuvette constituting a part of said flow path, said flow-through measuring cuvette including opposite first and second optically transparent surface parts defining an optical transmission path of the order of 0.5–2.0 mm, means for generating and irradiating said first optically transparent surface part of said flow-through measuring cuvette with multi-wavelength near infrared light so as to expose said whole blood stream flowing through said flow-through measuring cuvette to said multi-wavelength near infrared light, detector means for detecting the near infrared absorption spectrum of said whole blood stream flowing through said flow-through measuring cuvette represented by near infrared absorption data, and quantifying means for quantifying said content of said constituent by inputting said near infrared absorption data into a mathematical model representing the relation between near infrared absorption data and the content of said constituent.

The above objects, the above feature and the above advantage together with numerous other objects, features and advantages are in a fourth aspect of the invention obtained by an apparatus for determining the content of a constituent of blood of an individual, comprising:

means for extracting a whole blood stream of said individual from a blood vessel of said individual, a flow path, means for directing said whole blood stream through said flow path, a flow-through measuring cuvette constituting part of said flow path, said flow-through measuring cuvette including at least one optically transparent surface part, means for directing said whole blood stream through said flow path, means for propelling said whole blood stream through said flow path, causing said flow-path to flow through said flow path in a pulsed mode, monitor means for monitoring said flow of said whole blood stream through said flow-through measuring cuvette of said flow path, so as to determine periods of substantially constant flow of said whole blood stream flowing through said flow-through measuring cuvette, means for generating and irradiating said at least one optically transparent surface part of said flow-through measuring cuvette with electromagnetic radiation of a specific spectral composition, so as to expose said whole blood stream flowing through said flow-through measuring cuvette to said electromagnetic radiation of said specific spectral composition, detector means for detecting the electromagnetic radiation absorption spectrum, represented by electromagnetic radiation absorption data, of said whole blood stream flowing through said flow-through measuring cuvette at said periods of substantially constant flow of said whole blood stream flowing through said flow-through measuring cuvette, and quantifying means for quantifying said content of said constituent by inputting said electromagnetic radiation absorption data into a mathematical model representing the relation between electromagnetic radiation absorption data and the content of said constituent.

The above objects, the above feature and the above advantage together with numerous other objects, features and advantages are in a fifth aspect of the invention obtained by a method of hemodialysis, comprising:

extracting a whole blood stream of the order of 50–1,000 ml/min from a blood vessel of an individual, directing said whole blood stream through an extracorporeal flow path to a hemodialyser through a flow path comprising a flow-through measuring cuvette constituting part of said flow path, said flow-through ensuring cuvette including opposite first and second optically transparent surface part defining and optical transmission path of the order of 0.5–2.0 mm, irradiating said first optically transparent surface part of said flow-through measuring cuvette with multi-wavelength near infrared light comprising light of the wavelength range 700–1,800 nm such as 1,400–1,600 nm so as to expose said whole blood stream flowing through said flow-through measuring cuvette to said multi-wavelength near infrared light, detecting the near infrared absorption spectrum of said whole blood stream flowing through said flow-through measuring cuvette represented by near infrared absorption data, quantifying the content of urea of said whole blood stream by inputting said near infrared absorption data into a mathematical modal representing the relation between near infrared absorption data and the content of urea.

According to a sixth aspect of the present invention, a flow-through measuring cuvette is provided for use in either of the above methods or apparatuses said flow-through measuring cuvette defining a substantially non-varying flow-through area and including opposite, optically transparent surface parts defining a substantially non-varying optical transmission path of the order of 0.5–2.0 mm.

In accordance with the present invention, it has been realized that a whole blood/real-time determination of the content of a constituent of blood of an individual such as a patient suffering from kidney malfunction and being subjected to dialysis treatment my be carried out by a multi-wavelength near infrared analysis technique performed as a blood stream of the order of 50–1,000 mL/min is directed in its entirety through an optical transmission path of the order of 0.5–2.0 mm.

For handling the blood flow stream in question, the non-varying flow through area is preferably of the order of 5–20 $mm^2$, such as 12–17 $mm^2$, corresponding to the flow-through area of conventional dialysis tubing.

It has in accordance with the teachings of the present invention been realized that it is of the outmost importance that the blood of the whole blood stream which is analysed for determining the content of the constitutent in question of the blood of the individual in question should not be exposed to excessive pressure and/or velocity alterations or variations such as extreme acceleration or deceleration which inevitably result in deterioration or destruction of the blood of the individual in question.

The detection of the near infrared or alternatively the electromagnetic absorption spectrum which constitutes a basis for the quantifying of the content of the constituent in question may be based on transmission or reflection detection techniques in accordance with well known optical detection principles per se.

In a preferred embodiment of the invention the mathematical model allows for determination of several constituents at a time. The relevant constituents are selected from the group of urea, glucose, lactate, total protein, lipids, osmolality and hemoglobins.

According to the presently preferred embodiments of the second and fourth aspect of the present invention, the detection of the electromagnetic radiation absorption spectrum is based on a transmission detection of the electromagnetic radiation transmitted through the blood flow stream flowing through the substantially non-varying optical transmission path as the flow-through measuring cuvette comprises opposite first and second optically transparent surface parts and defines a substantially non-varying optical transmission path, and as the detection of the electromagnetic radiation absorption spectrum is determined by detecting the transmission of the electromagnetic radiation through the whole blood stream flowing through the flow-through measuring cuvette through the optical transmission path thereof.

The cuvette which constitutes the above sixth aspect of the present invention and which also constitutes an element of the methods and apparatuses according to the above first, second, third, fourth and fifth aspects of the present invention preferably constitutes an element fulfilling the above requirements as to low or substantially low pressure or velocity impact to the blood which is guided through the cuvette. Thus, the flow-through cuvette according to the present invention preferably comprises a central section including said opposite first and second optically transparent surface parts, tubular inlet and outlet sections and first and second transition sections, said first and second transition sections constituting sections connecting said inlet and outlet sections, respectively, to said central section and presenting gradually changing sectional shapes generating to no substantial extent pressure or velocity gradients to said whole blood stream flowing through said flow-through cuvette so am to eliminate to any substantial extent any blood degradating pressure or velocity impact to said blood flow.

According to the presently preferred embodiments of the above aspects of the present invention, the detection of the absorption spectrum being a near infrared absorption spectrum or alternatively another electromagnetic absorption spectrum of the whole blood stream flowing through the flow-through measuring cuvette preferably comprises detecting the spectrum represented by a first sat of spectral data of light transmitted through the whole blood stream flowing through the flow-through measuring cuvette and irradiated from the second optically transparent surface part of the flow-through measuring cuvette.

The detection of the absorption spectrum may be based on a previous detection of the spectral composition of the radiation irradiated to the flow-through measuring cuvette. Alternatively and preferably, the detection of the absorption spectrum of the whole blood stream flowing through the flow-through measuring cuvette preferably comprises detecting the spectrum represented by a second set of spectral data of the electromagnetic radiation irradiated to the first optically transparent surface part of the flow-through measuring cuvette thus rendering it possible to compensate for any variation of the radiation caused by for example ageing of the radiation source.

The detection of the absorption spectrum preferably further comprises generating the absorption data representing the absorption spectrum in question from the first set of spectral data and from the second sot of spectral data, thus compensating for any radiation source changing or ageing effects. The generation of the absorption data from the first and second sets of spectral data is preferably performed by subtracting the first sat in logaritmic representation from the second set in logaritmic representation, thus providing the absorption data.

In accordance with optical detection techniques well known in the art, the detection of the absorption spectrum of the whole blood stream flowing through the flow-through measuring cuvette preferably further comprises detecting the spectrum represented by a third set of spectral data of light irradiated from the second optically transparent surface part of the flow-through measuring cuvette at periods of time in which the first optically transparent surface of the flow-through measuring cuvette is not irradiated. The third set of spectral data, thus, represents a reference state, i.e. a state under which no radiation should be detected. The third set of spectral data, thus, constitutes a darkness reference data not which further provides zero current compensation of the detector or detectors used for detecting the radiation.

The darkness compensation and zero current compensation technique preferably further comprises subtracting the third set of spectral data from both the first set of spectral data and from the second set of spectral data, thereby providing corrected first and second sets of spectral data from which the absorption data is provided as previously discussed.

The detection of the absorption spectra being near infrared absorption spectra or alternatively electromagnetic absorption spectra is based on spectrophotometrical measuring technique. The spectrophotometrical measuring technique may be performed in accordance with numerous spectrophotometric techniques well known in the art, such as FT (Fourier transformation) spectrophotometric technique, Hadamard transformation spectrophotometric technique, AOTF (Acoustic Optical Tunable Filter) spectrophotometric technique, diode array spectrophotometric technique including reverse optical measuring technique, scanning dispersive spectrophotometric technique or similar spectrophotometric technique.

The mathematical model on the basis of which the content of the constituent in question is quantified is preferably established on the basis of a training sat of samples having relevant known variations in composition and thus producing relevant absorption spectra. The quantifying of the content of the constitutent in question preferably comprises mathematical analysis techniques such as multivariate data analysis technique, e.g. PLS analysis technique (Partial Least Square), PCR analysis technique (Principal Components Regression), MLR analysis technique (Multiple Linear Regression), artificial neural network analysis technique or similar analysis technique. The mathematical quantifying technique may be performed in accordance with the technique described in U.S. Pat. No. 4,975,581 to which reference is made and which is hereby incorporated in the present specification by reference.

According to the fifth aspect of the present invention, the dialysis treatment may be controlled on the basis of the determination of the content of urea of the whole blood stream as the hemodialysis treatment may be continued until the content of urea of the whole blood stream is decreased below a specific threshold.

The spectrophotometrical detection technique is preferably as will be evident from the below detailed description performed in accordance with the teaching described in U.S. Pat. No. 4,977,281, to which reference is made and which is hereby incorporated in the present specification by reference. Relevant and interesting detection and measuring techniques are disclosed in U.S. Pat. No. 5,105,054, U.S. Pat. No. 4,745,279, U.S. Pat. No. 4,717,548, U.S. Pat. No. 4,056,368, EP 0 495 503, EP 0 457 804, EP 0 419 223, EP 0 419 222, EP 0 238 809, DE 2825134. Reference is made to the above U.S., EP and DE patents and the above U.S. patents are hereby further incorporated in the present description by reference.

BRIEF DESCRIPTION OF THE DRAWING

The invention will now be further described with reference to the drawings, in which FIG. 4 is a perspective view of a supply pump of a hemodialysis machine also illustrating a measuring cuvette of the whole blood analyzing apparatus shown in FIG. 1 and further a pulse detector, FIG. 5 is a perspective and schematic view of a light-transmitting assembly, FIG. 6 is a perspective and schematic view of a light-reflecting assembly, FIG. 14 is a perspective view of the measuring cuvette of the whole blood analyzing apparatus shown in FIG. 1.

In FIG. 1, a prototype embodiment of a whole blood analyzing apparatus is shown implemented in accordance with the teaching of the present invention. The blood analyzing apparatus is shown in the upper part of FIG. 1 and comprises a dual beam chopper section 100, shown in the uppermost part of FIG. 1 and shown in greater details in FIG. 2, a spectrophotometric section, shown in the central part of FIG. 1 and shown in greater details in FIG. 3, a computer section comprising a personal computer, shown in the central, right-hand part of FIG. 1, for carrying out a data processing of data produced by the spectrophotometric section, in accordance with the analyzing technique known as partial least-square methods for spectral analysis, vide e.g. references 1, 2 and 3, and a measuring cuvette 24, shown in the central part of FIG. 1 below the spectrophotometric section and also shown in greater details in FIG. 14. The cuvette 24 is interfaced between the dual beam chopper section 100 and the spectrophotometric section and is interconnected between a hose pump or peristaltic pump 50 and a dialysis apparatus 10, which hose pump 50 supplies blood from a patient to the dialysis apparatus 10. The hose pump 50 and the dialysis apparatus 10 are shown in the lowermost part of FIG. 1. The dialysis apparatus 10 comprises a conventional dialysis machine 40, which communicates with a blood vessel of a patient or parson who needs dialysis treatment. The reference numeral 12 designates a forearm of the patient or person in question.

Figure 1:
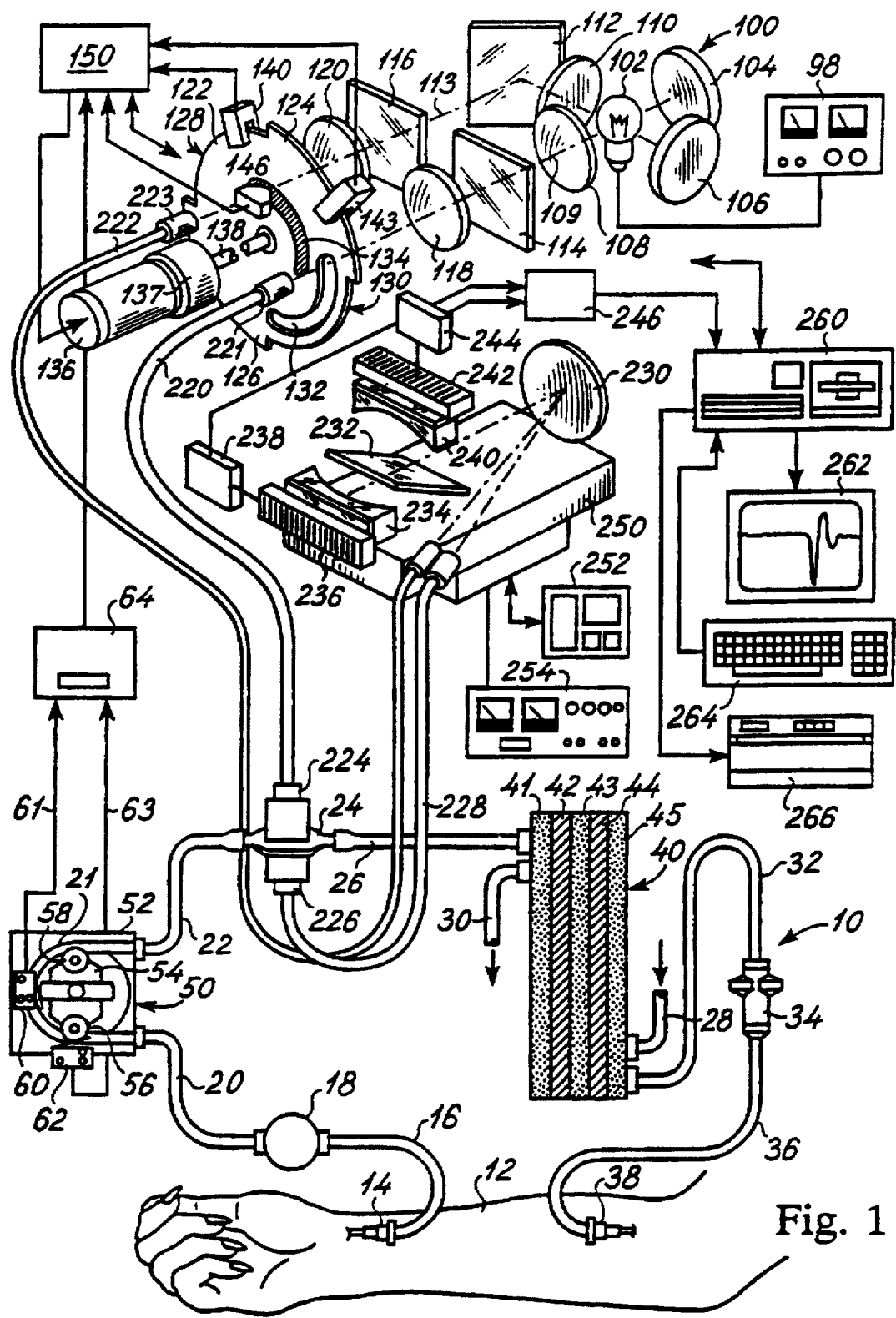
FIG. 1 is a schematic vie of a whole blood analyzing apparatus illustrating the intentional application of the whole blood analyzing apparatus in connection with monitoring a hemodialytic process.

From the forearm 12 of the patient or person, blood is extracted through a cannula 14 and supplied through a hose 16 to an arterial pressure monitor 18 and further through a hose 20 to the hose pump 50. The hose pump 50 comprises a housing 52, in which the hose 20 is received, defining a hose loop 21 communicating with propelling pressure rollers 56 and 58 supported on a pressure-roller support body 54 of the hose pump 50.

The hose 20 and the hose loop 21 further communicates with a hose 22, establishing connection to the cuvette 24, through which the blood extracted from the forearm 12 is guided in a laminar flow of no substantial pressure or volume flow reduction further to a hose 26, through which the blood is input to the dialysis machine 40 of the dialysis apparatus 10, in which dialysis machine the blood in rinsed an the blood communicates with a dialysis fluid through hemodialysis membranes in accordance with the hemodialysis technique well-known in the art per se.

The dialysis fluid in input to the dialysis machine 40 through an inlet hose 28 and output from the dialysis machine 40 through an outlet hose 30. The blood, which has been subjected to hemodialysis treatment in the dialysis machine 40, is output from the dialysis machine 40 through a further hose 32, which supplies the partly rinsed blood to an air and foam detector 34, serving the purpose of preventing that air bubbles or foam are present in the blood, which is returned through a hose 36 and a cannula 38 to a blood vassal at the forearm 12 of the patient or person in question.

The dialysis fluid and the blood input to the hemodialysis machine 40 are guided through the hemodialysis machine 40 in counterflow. Within the dialysis machine 40, separate components are defined, which are designated the reference numerals 41, 42, 43, 44 and 45. The compartments 41, 43 and 45 constitute compartments in which the blood is forced in counterflow in relation to the dialysis fluid, which is forced through the compartments 42 and 44 from the inlet hose 28 to the outlet hose 30.

The cuvette 24, which in shown in greater details in FIG. 14, constitutes a central or essential component of the whole blood analyzing apparatus. The configuration of the cuvette prevents that the blood is accelerated, decelerated or subjected to pressure or volumetric gradient, which might cause severe damage to the blood cells of the blood. The cuvette is further adapted for NIR infrared spectrophotometric analysis of the blood for analyzing the constituents of the blood and consequently for monitoring the hemodialysis process, which is carried out by means of the dialysis machine 40. By the monitoring and analyzing of the hemodialysis operation, a more adequate and efficient hemodialysis operation may be carried out, since the hemodialysis operation may be carried out for a period of the necessary to reduce the contents of specific blood constitutents to levels below preset threshold levels. Furthermore, the continuous monitoring and analyzing technique which may be carried out by means of the whole blood analyzing apparatus implemented in accordance with the teaching of the present invention renders it possible to stop the hemodialysis operation as the above threshold levels have bean reached, contrary to the conventional hemodialysis operation, in which the hemodialysis operation is carried out for a period of time which is based on a pure estimate based on a blood sample analysis and empirical realizations regarding the relations between hemodialysis time periods and reductions of the contents of specific blood constituents.

The cuvette 24 in of a structure in which the optical path in of the order of 1 mm, rendering it possible to carry out a NIR infrared spectrophotometric analysis of the blood which is caused to flow through the cuvette 24 without any substantial pressure gradients being generated by the presence of the cuvette 24 within the blood supply line from the hose pump 50 to the dialysis machine 40.

The hose pump 50 in shown in greater details in FIG. 4. The roller support body 54 of the hose pump 50 in caused to rotate, as the roller support body 54 is connected to a shaft 53 of a motor 51. As the roller support body 54 is caused to rotate in the clockwise direction in FIGS. 1 and 2, the blood is caused to be forced from the hose 20, which constitutes a blood inlet hose, through the hose loop 21 and further through the hose 22, which constitutes an outlet tube, towards the cuvette 24.

The position of the roller body 54 and consequently the rollers 56 and 58, propelling the blood through the hose loop 21, in detected by means of a stem body 59, which constitutes an integral, outwardly protruding part of the roller support body 54, and which engages with two switches 60 and 62, serving the purpose of providing electrical signals representing the position of the stem body 59 and consequently the position of the roller support body 54.

The switches 60 and 62 generate pulses, which constitute pulse trains representing the actual position of the rollers 54 and 56 and further the rotational notion of the roller support body 54. The switches 60 and 62 are arranged so as to generate pulses as the stem body 59 engages with the switch in question, said pulses representing the position of the roller support body 54, in which a pressure wave is generated in the blood supplied from the hose pump as the rollers 56 and 58 are disengaged from the hose loop 21.

The pulses generated by the switches 60 and 62 are supplied through electrical signal lines 61 and 63, respectively, to a PLL (phase locked loop) synchronizing circuit block 64, the purpose of which will be evident from the below description.

Figure 2:
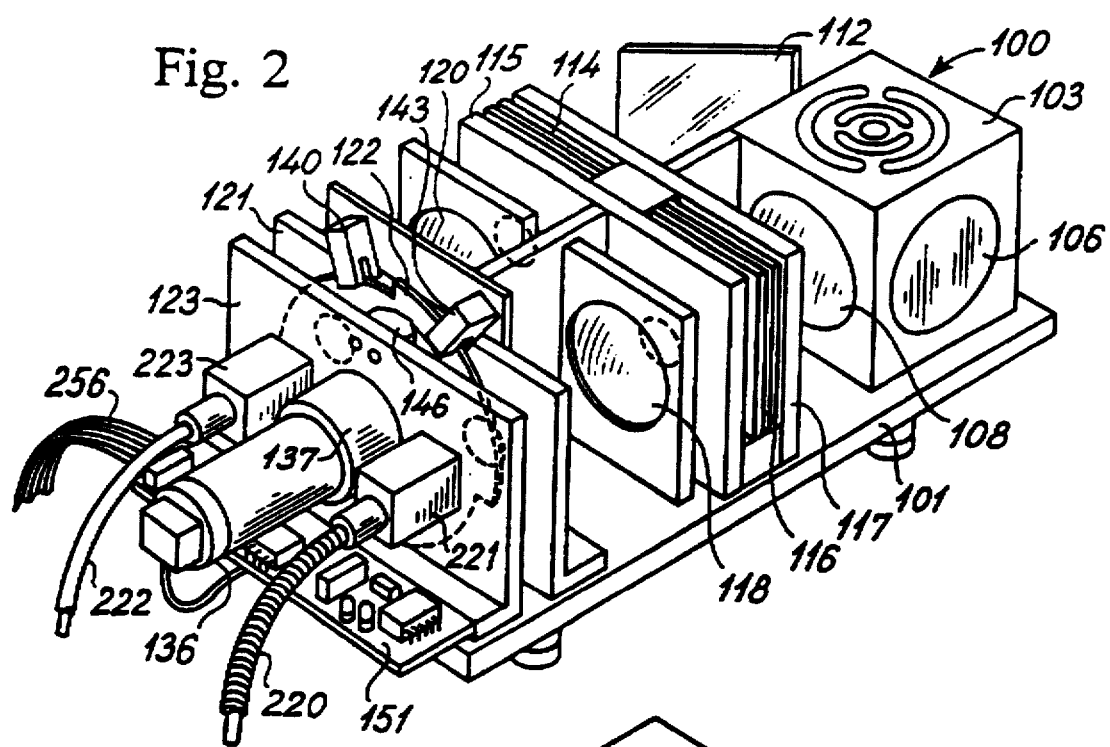
FIG. 2 is a perspective view of a beam-splitting chopper section of the whole blood analyzing apparatus shown in FIG. 1.

The dual beam chopper section 10, shown in the uppermost part of FIG. 1 and further in FIG. 2, comprises a light-generating lamp 102, preferably constituted by a halogen bulb generating visible light, i.e. electromagnetic radiation within the wavelength interval 400–700 nm, NIR (NIR infrared radiation), i.e. electromagnetic radiation within the wavelength interval 700–2500 nm and IR (infrared radiation), i.e. electromagnetic radiation within the wavelength interval 2500–10000 nm. The lamp 102 is supplied from a power supply 98.

The electromagnetic radiation generated by the lamp 102 is focussed in two light beams, a first one of which is generated by means of a mirror 104 and a focusing lens 108, and a second one of which in generated by means of a mirror 106, similar to the mirror 104, a lens 110, similar to the lens 108 and a mirror 112. The first light beam is designated the reference numeral 109 and is directed from the lens 108 through a filter 114, removing electromagnetic radiation from the wavelength range 200–450 nm, and is directed through a further focussing lens 118. The second light beam is designated the reference numeral 113 and is directed through a filter 116, similar to the filter 114, and is further directed through a further focusing lens 120, similar to the focusing lens 118.

The first light beam 109 and the second light beam 113 focussed by means of the focussing lenses 118 and 120, respectively, are chopped by means of a chopper disc 122. The chopper disc 122 serves the purpose of allowing transmission of the first and the second light boom to a respective optical fibre and of interrupting the light beams and consequently preventing light from being transmitted to the optical fibre in question. For generating the light-beam chopper effect, the chopper disc 122 is provided with a slit 132, which constitutes a 90° segment of the chopper disc. The chopper disc 122 in caused to rotate, driven by a motor assembly 136, which is provided with a gear assembly 137, serving the purpose of reducing the rotational speed of a motor shaft of the motor assembly 136 to a fairly low rotational speed of an output shaft of the gear assembly 137, on which output shaft the chopper disc 122 is mounted. The chopper disc in caused to rotate at a rotational speed of approximately 50–250 rpm in dependency of the operation of the hose pump. As the chopper disc 122 rotates, the light beams 109 and 113 are sequentially transmitted to a first optical fibre 220 and a second optical fibre 222, respectively. For receiving the light beams 109 and 113, the optical fibres 220 and 222 are provided with optical fibre fittings 221 and 223, respectively.

Apart from the light-transmitting slit 132, the chopper 122 is provided with a light-reflecting surface area 134 and two outwardly protruding rim parts 124 and 126, which are separated by circumferential recesses 128 and 130. The outwardly protruding rim parts 124 and 126 and the circumferential recesses 128 and 130 communicate with two detectors 140 and 143, which serve the purpose of detecting the presence of outwardly protruding rim parts 124 and 126 received within the detector in question. The detectors 140 and 143 are based on the optical principle as will be evident from the below description of the detectors 140 and 143, which are shown in greater details in FIG. 8. The detectors 140 and 143 may be based on different detector principles, such as capacitive, inductive or proximity detector principles.

Figure 8:
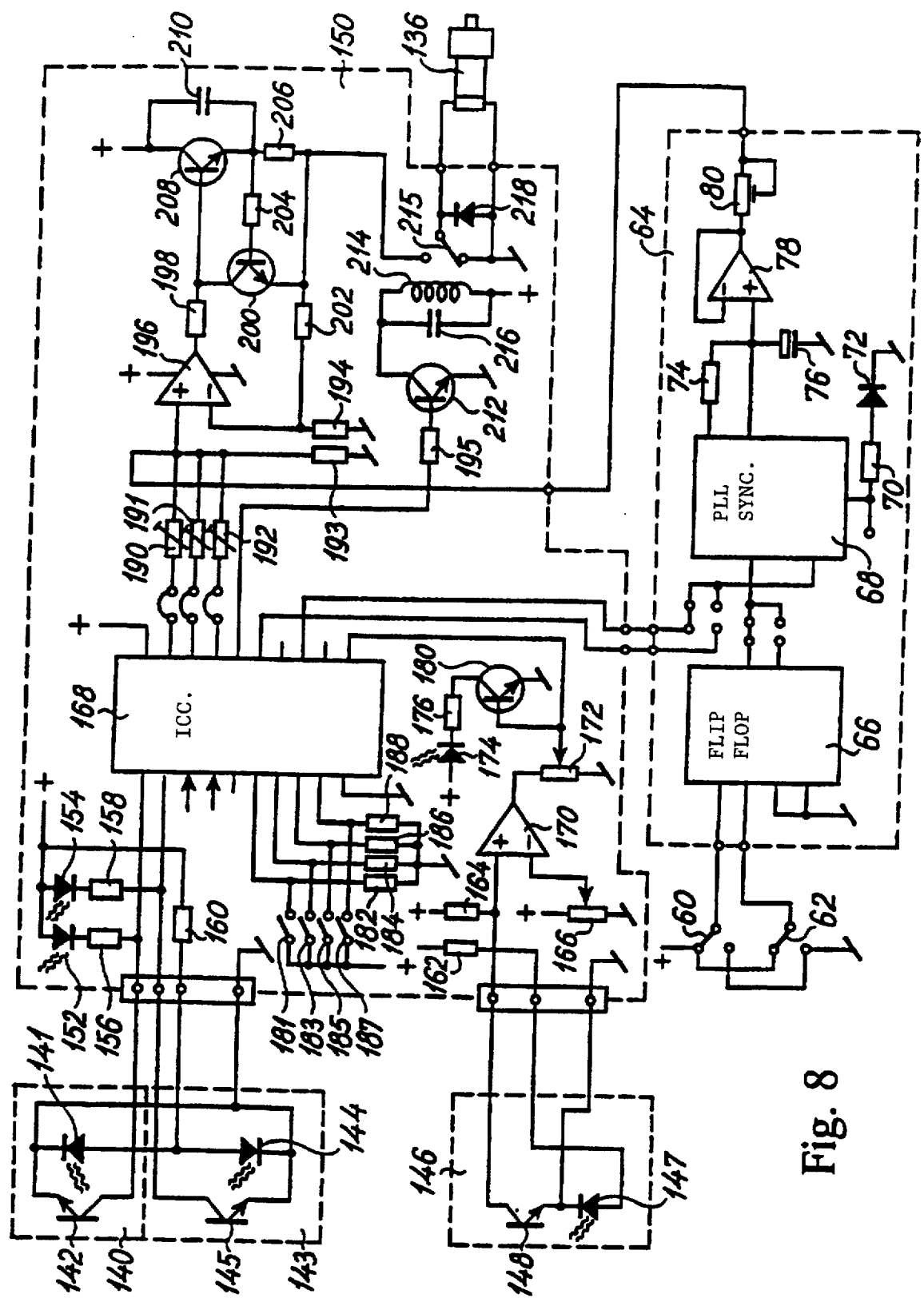
FIG. 8 is a diagrammatic view of an electronic circuitry section of the dual beam chopper section shown in FIG. 2, FIGS. 9–13 are diagrammatic views of spectra recorded by means of the whole blood analyzing apparatus shown in FIG. 1.

The light-transmitting surface area 134 communicates with a further detector 146, which constitutes a detector, including a light source and a light detector, and which is also in greater details in FIG. 8.

The detectors 140, 143 and 146 serve the overall purpose of generating pulses representing the actual position of the chopper disc 122. The pulses generated by the detectors 140, 143 and 146 are input to a detector circuit block 150, which also communicates with the PLL synchronizing circuit block 64, and controls the rotation of the motor assembly 136. The detector circuit block 150 further communicates with the CPU of a personal computer 260, which CPU performs the data processing of the data generated by the spectrophotometric section of the whole blood analyzing apparatus and performs the overall control of the operation of the apparatus.

The light beam 109 transmitted to the optical fibre fitting 221 and further through the optical fibre 220 is emitted from an optical fibre fitting 224 and transmitted through the cuvette 24 and the blood present within the cuvette 24. The light transmitted through the blood within the cuvette 24 is received by means of an optical fibre fitting 226 and in further transmitted through an optical fibre 228 to the spectrophotometric section shown in the central part of FIG. 1 below the above-described dual beam chopper section 100.

Figure 3:
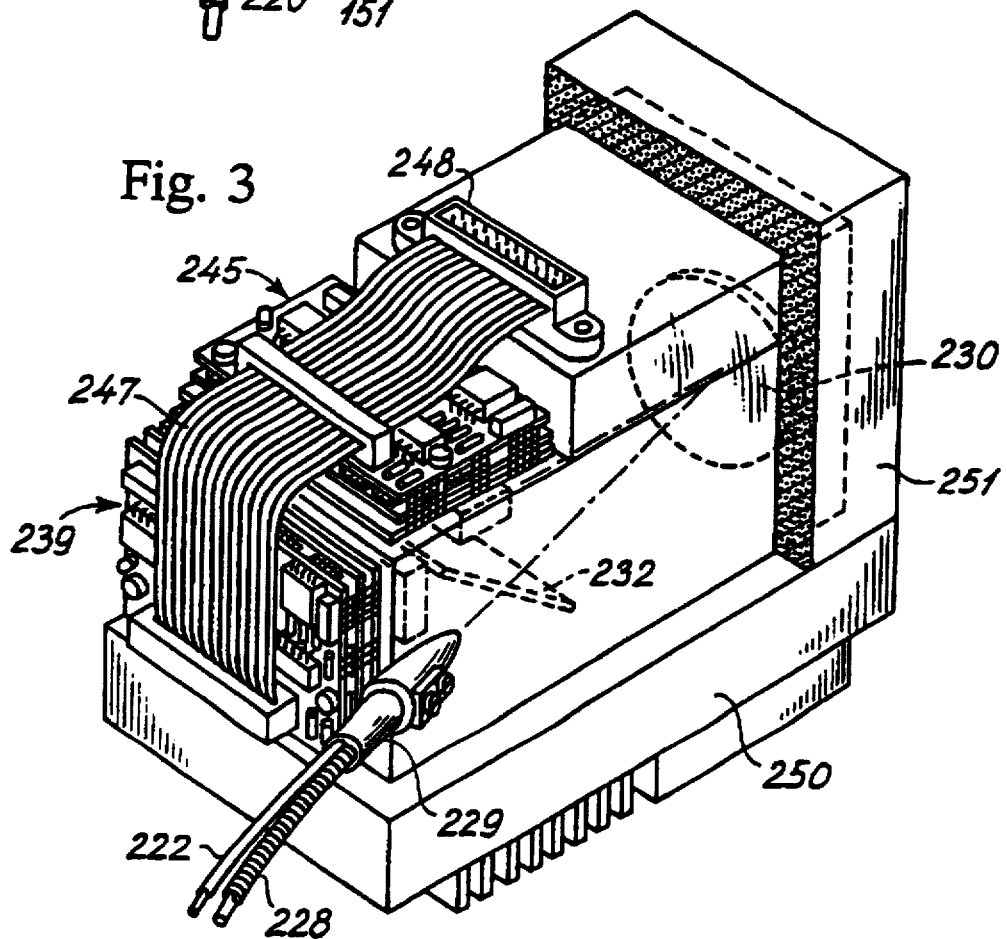
FIG. 3 is a perspective view of a spectrophotometric section of the whole blood analyzing apparatus shown in FIG. 1.

The light beam 113 transmitted to the optical fibre fitting 223 and further through the optical fibre 222 is also transmitted to the spectrophotometric section. The optical fibre 222 constitutes a reference light-transmitting optical fibre. The optical fibre 222 is of the same length as the optical fibres 220 and 228 in order to eliminate any influence from differences in optical fibres giving origin to optical fibre length-dependent attenuation. The optical fibres 228 and 222 have their output ends received within an optical fibre connector 229, which is shown in FIG. 3, which directs the light received from either of the two optical fibres 228 and 222 to a concave holographic grating 230 of the spectrophotometric section. The spectrophotometric section is preferably constituted by a spectrophotometer as described in U.S. Pat. No. 4,997,281, to which reference made, and which is herewith incorporated in the present specification by reference.

The light beam emitted from the optical fibre connector 229 and originating from one of the fibres 228 and 222 is reflected from the mirror 230 and transmitted through a beam-splitting mirror 232 and focussed by means of lenses 234 and 240 on first and second optical detectors 236 and 242, respectively. The first and second optical detectors 236 and 242, respectively, are sensitive and responsive to electromagnetic radiation within the wavelength interval 520–1100 nm and 1030–1800 nm, respectively, and are constituted by an array of silicon photodiodes and array germanium photodiodes, respectively. Each of the arrays contains 76 diodes together providing a 152 incremental representation of the wavelength interval 520–1800 nm.

The first optical detector 236 is connected to a optical detector circuit block 238, including a multiplexing circuit serving the purpose of sequentially presenting the output signals generated by the photodiodes of the array of photodiodes of the optical detector 236 to an input of an A/D converter 246. Similarly, the second optical detector 242 is connected to an optical detector circuit block 244, including a multiplexing circuit, also serving the purpose of sequentially presenting the output signals generated by the photodiodes of the array of photodiodes of the optical detector 242 to an input of the A/D converter 246.

The A/D converter 246 is through its output connected to an input of the CPU of the personal computer 260. The A/D converter 246 is also supplied with measuring signals supplied through multiplexing input circuits and representing additional measuring parameters, such as the temperature of the spectrophotometric section block and generated by means of a temperature detector.

The components of the spectrophotometric section block are supported on a support block 250, which constitutes a base plate of a thermally insulating encasing or housing, not shown in FIG. 1, which is thermostatically controlled by means of a thermostatic controller 252 to a temperature of 16° C. The electronic circuitry of the spectrophotometric section block is powered from a power supply 254.

In FIG. 4, the hose pump 52 and the pivot 24 together with the optical fibres 220 and 228 connected to the cuvette 24 through the optical fibre fittings 224 and 226, respectively, are shown together with a pulse detector 86, which is mounted on the hose 26 or alternatively mounted on the hose 22 adjacent the cuvette 24. The pulse detector 86 is provided with electrical wires 82 and 84 for establishing electrically conductive connection to the PLL synchronizing circuit block 64, shown in FIG. 1, end for supplying electrical signals thereto, representing the blood flow through the detector and further the variation of the blood flow through the hose 26, on which the pulse detector 86 is mounted, and consequently through the cuvette 24, caused by the pressure fluctuations generated by the hose pump 52, an discussed above. The pulse detector 86 may be based on inductive or capacitive detector principles or alternatively based on optical detection technique, as the pulse detector 86 may comprise light-generating means and light-detecting means monitoring the blood flow through the pulse detector based on optical transmission principles or optical reflection principles or may further alternatively constitute a fibre optic connector, to which two optical fibres are connected, said optical fibres substituting the electrical wires 82 and 84.

In FIG. 5 an alternative light transmission technique is shown, as the cuvette 24 is omitted. The hoses 22 and 26 constitute an integral home which is clamped between the optical fibre connectors 224 and 226, defining a shallow hose segment 90 of a configuration similar to that of the cuvette 24, as the optical fibre connectors 224 and 226 are fixated by means of a clamping device 225 so an to define a specific spacing between the output end of the optical fibre fitting 224 and the input and of the optical fibre fitting 226.

FIG. 6 illustrates a further, alternative, optical detector technique, according to which the light transmission technique implemented by means of the optical fibres 222 and 228 is substituted by an optical detector implemented in accordance with the optical reflection technique. In FIG. 6, an optical detector 92 is shown, which is mounted an the hose 26 and comprises an input optical fibre 94 and an output optical fibre 96, which optical fibres detect electromagnetic radiation radiated from the output and of the optical fibre 94 and reflected from the blood flown through the optical detector 92. The optical detector 92 may constitute a component substituting the pulse detector 86, shown in FIG. 4, or alternatively constitute a component replacing the optical transmission detector comprising the optical fibres 222 and 228, the optical fibre connectors 224 and 226, respectively, and further the cuvette 24.

In an alternative embodiment of the optical detector 92, the optical detector communicates with a cuvette, such as the cuvette 24, shown in FIGS. 1 and 4 and further in FIG. 14, or an alternative cuvette structure adapted to allow the blood to flow through the cuvette without any substantial pressure or volumetric variations.

In FIG. 2, the dual beam chopper section 100 is shown in greater details further illustrating a supporting plate 101, on which an optical housing 103 is mounted. The optical housing 103 includes the lamp 102, the mirrors 104 and 106 and the lenses 108 and 110. FIG. 2 further illustrates two filter supports 115 and 117, which support the filters 114 and 116, described above FIG. 2 further illustrates the journalling of the chop-per disc 122, which is sandwiched between two brackets 121 and 123, which also serve the purpose of supporting the optical fibre fittings 221 and 223 and suer the gear assembly 137, the output shaft 138 of which is connected to the chopper disc 122, as the chopper disc 122 is mounted on the output shaft 138. In FIG. 2, a printed circuit board 151 is shown, which constitutes the printed circuit board of the detector circuit block 150, shown in FIG. 1 and shown in greater details in FIG. 8.

In FIG. 3, the spectrophotometric section block is shown. Apart from the optical fibres 222 and 228 and the optical fibre connector 229, the concave holographic grating 230 and the beam-splitting mirror 232 are shown. The reference numeral 251 designates a bracket which is rigidly connected to the support plate 250 of the spectrophotometer, and the reference numerals 239 and 245 designate printed circuit boards containing the electronic circuitry of the first and second optical detector circuit blocks 238 and 244, respectively, shown in FIG. 1. The reference numeral 247 designates a multicore cable which interconnects the printed circuit boards 239 and 245 and is further connected to a multipin socket 248 for receiving a mating multipin plug for establishing electrically conductive connection with the CPU of the personal computer 260.

Figure 7:
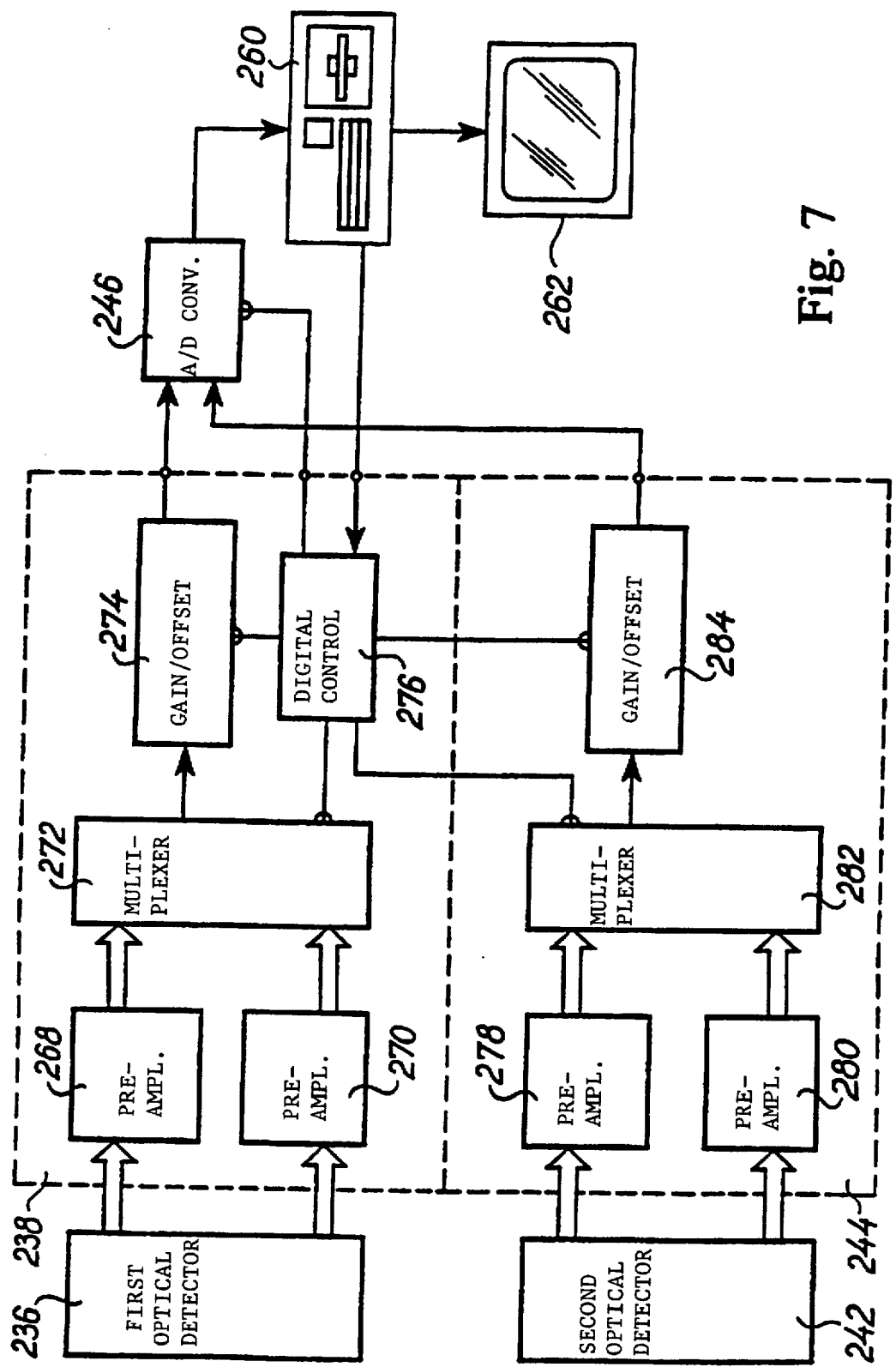
FIG. 7 is a block diagrammatic view of the electronic circuitry of the spectrophotometric section shown in FIG. 3.

FIG. 7 in a block diagram of the electronic circuitry of the spectrophotometric section shown in the central part of FIG. 1, and further shown in FIG. 3. In FIG. 7, the first optical detector 236 is connected to the first optical detector circuit block 238, which is shown in dotted line in the uppermost part of FIG. 2 and which comprises two multichannel preamplifier blocks 268 and 270, the inputs of which are connected to respective diodes of the diode array of the first optical detector 236. The outputs of the multichannel preamplifier blocks 268 and 270 are connected to respective inputs of a muliplexer block 272, the outputs of which are connected via an optional programmable gain and offset block 274 to the A/D converter block 246, shown in FIG. 1. The control input of block 274 is connected to a control output of a digital control block 276. A control input of the digital control block 276 is connected to the CPU 260 of the personal computer controlling the overall operation of the whole blood analyzing apparatus. The A/D converter 246 is also controlled by the digital control block 276 through a separate control input, which is connected to a control output of the digital control block 276.

In the lowermost part of FIG. 7, the second optical detector 242 is shown, which is connected to the second optical detector block 244. The second optical detector block 244 is of a topographical configuration similar to that of the first optical detector block 238 and comprises two multichannel preamplifier blocks 278 and 280 corresponding to the multichannel preamplifier blocks 268 and 270 described above, which are further connected to a multiplexer block 282 similar to the multiplexer block 272 of the first optical detector circuit block 238. The multiplexer block 282 in via an optional programmable gain and offset block 284 similar to the block 274 connected to the A/D converter block 246, shown in FIG. 1. The optional programmable gain and offset block 284 of the second optical detector circuit block 244 is controlled by the digital control block 276, which is shared by the two optical detector circuit blocks 238 and 244. The multiplexer block 282 is like the Multiplexer block 272 controlled by the digital control block 276.

The electronic circuitry shown in FIG. 7 is further described in U.S. Pat. No. 4,997,281, to which reference is made, and which is hereby incorporated in the present specification by reference.

FIG. 8 is a block diagram of the detector circuit block 150, the PLL synchronizing circuit block 64 and further the detectors 140, 143 and 146. In the upper left-hand part of FIG. 8, the detectors 140 and 143 are shown, each comprising a light-emitting diode 141 and 144, respectively, and a phototransistor 142, 145, respectively. The emitter of the phototransistors 142 and 145 are connected through series configurations of a light-emitting diode 152 and 154, respectively, and a resistor 156 and 158, respectively, to a positive supply rail of the detector circuit block 150, and the emitters of the phototransistors which constitute NPN transistors are grounded. The light-emitting diodes 141 and 144 have their anodes connected through a common series resistor 160 to the positive supply rail and have their cathodes grounded.

As one of the phototransistors 142 and 145 receives light emitted from the light-emitting diode 141 and 144, respectively, the phototransistor in question starts conducting and causes the potential of the collector of the phototransistor in question to be lowered from the voltage of the positive supply rail, causing a shift of a respective detector input pin of a integrated circuit control block 168. The resistors 156 and 158 constitute pull-up resistors, which cause the inputs of the integrated circuit control block 158 connected to the collectors of the phototransistors 162 and 164 to be pulled up to the voltage of the positive supply rail, to which the resistors 156 and 158 are connected through the LEDs 152 and 154, respectively, provided the phototransistors 142 and 145 are not in their conductive states. The integrated circuit control block 168 is provided with addition control inputs, which are connected through pull-down resistors 182, 184, 186 and 188 to ground and further through switches 181, 183, 185 and 187, respectively, to the positive supply rail of the detector circuit block 150. The switches 181 and 183 are provided for inverting the signals output from the integrated circuit block 168 to the PLL synchronizing circuit block 64 to be described in greater details below. The switches 185 and 187 are provided for debugging purposes.

The detector 146 is, like the detectors 140 and 143, provided with a light-emitting diode 147 and a phototransistor 148. The anode of the light-emitting diode 147 is connected to the positive supply rail of the detector circuit block 150 through a resistor 162, and the junction of the cathode of the light-emitting diode 147 and the emitter of the phototransistor 148, which of an NPN configuration, are connected to the ground.

The collector of the phototransistor 148 is connected through a pull-up resistor 164 to the positive supply rail and further connected to the non-inverting input of an operational amplifier 170. The inverting input of the operational amplifier 170 is connected to an offset compensation potentiometer 166, which is interconnected between the positive supply rail of the detector circuit block 150 and the ground. The output of the operational amplifier 170 is connected through a potentiometer 172 to the ground, and the wiper of the potentiometer 172 is connected to the bass of an NPN transistor 180, the emitter of which is grounded, and the collector of which is connected to the positive supply rail through the series configuration of a light-emitting diode 174 and a resistor 176. The wiper of the potentiometer 172 is also connected to a control input pin of the integrated circuit control block 168.

In the lower part of FIG. 8, the PLL synchronizing circuit block 64 is shown, which is connected to the switches 60 and 62, mounted an the stem body 54 of the hose pump 50, serving the purpose of detecting the rotational operation of the roller support body 54 of the hose pump 50, as described above. The switches 60 and 62 are switchable between inoperative states, in which the switches connect the positive supply rail of the overall eletronic circuitry of the whole blood analyzing apparatus to control inputs of an integrated circuit 66, constituting a flip-flop circuit, and operative states, in which the switches connect the control inputs of the integrated circuit 66 to the ground. The output of the integrated circuit 66 is connected to a signal input of a PLL synchronizing chip 68, which further has its compensation input connected to a control output of the integrated circuit control block 168 of the detector circuit block 150. A SNP output terminal of the integrated circuit 68 is connected through a series configuration of a resistor 70 and a diode 22 to the ground. An output terminal of the integrated circuit 68 is connected to an VCO input of the integrated circuit 68 through a resistor 74 and further grounded through a capacitor 76. The VCO input of the integrated circuit 68 is further connected to a non-inverting input of an operational amplifier 78, which is operated in a unity-gain non-inverting mode, as the output of the operational amplifier 78 is short-circuited to the inverting input of the operational amplifier 78. The output of the operational amplifier 78 is connected through a variable resistor 80 to junction at the non-inverting input of an operational amplifier 196 of the detector circuit block 150, the non-inverting input of which is further connected through variable resistors 190, 191 and 192 to output control terminals of the integrated circuit control block 168 and grounded through a resistor 193.

The output of the operational amplifier 196 is connected through a resistor 198 to the bass of an NPN Darlington power transistor 208, the collector of which is connected to the positive supply rail of the detector circuit block 150, and the emitter of which is connected through a series resistor 206 to a pin of a relay contact 215, which in its operative state supplies current through the NPN Darlington power transistor 208 and the resistor 206 to the motor 136. The collector and the emitter of the NPN Darlington power transistor 208 are short-circuited through a capacitor 210 constituting a noise-suppression capacitor. The emitter of the NPN Darlington power transistor 208 is further connected through a resistor 204 to the base of a NPN transistor 200, the collector of which is connected to the base of the NPN Darlington power transistor 208, and the emitter of which is connected to the relay contact of the relay 215. The transistor 200 constitutes a feedback current-limiting transistor, the emitter of which is connected through a resistor 202 to the inverting input of the operational amplifier 196, the inverting input of which is further grounded through a resistor 194.

The relay contact 215 is activated by means of a relay coil 214, provided the integrated circuit detector block 168 shifts a separate motor output low, which output is connected through a resistor 195 to the base of a NPN relay turn-on resistor 212, the emitter of Which is grounded, and the collector of which is connected to one terminal of the relay coil 214, the other terminal of which is connected to the positive supply rail of the detector circuit block 150.

The terminals of the relay coil 214 are further short-circuited through a noise-suppressing capacitor 216. Provided that the relay coil 214 is not energized, the relay contact 215 short-circuits the motor 136. A surge-suppression diode 218 is further provided, short-circuiting the terminals of the motor 136.

FIGS. 9, 10, 11, 12 and 13 are diagrams illustrating print-outs produced from the measurement of sample fluids which are analyzed by means of the whole blood analyzing apparatus according to the present invention.

In FIGS. 9, 10, 11, 12 and 13 the abscissa axis represents the pixel number 0–151 corresponding to the near infrared wavelength interval 520–1800 nm represented by a total of 152 pixels i.e. providing a 152 incremental wavelength interval representation of the above 520–1800 nm wavelength interval.

Figure 9:
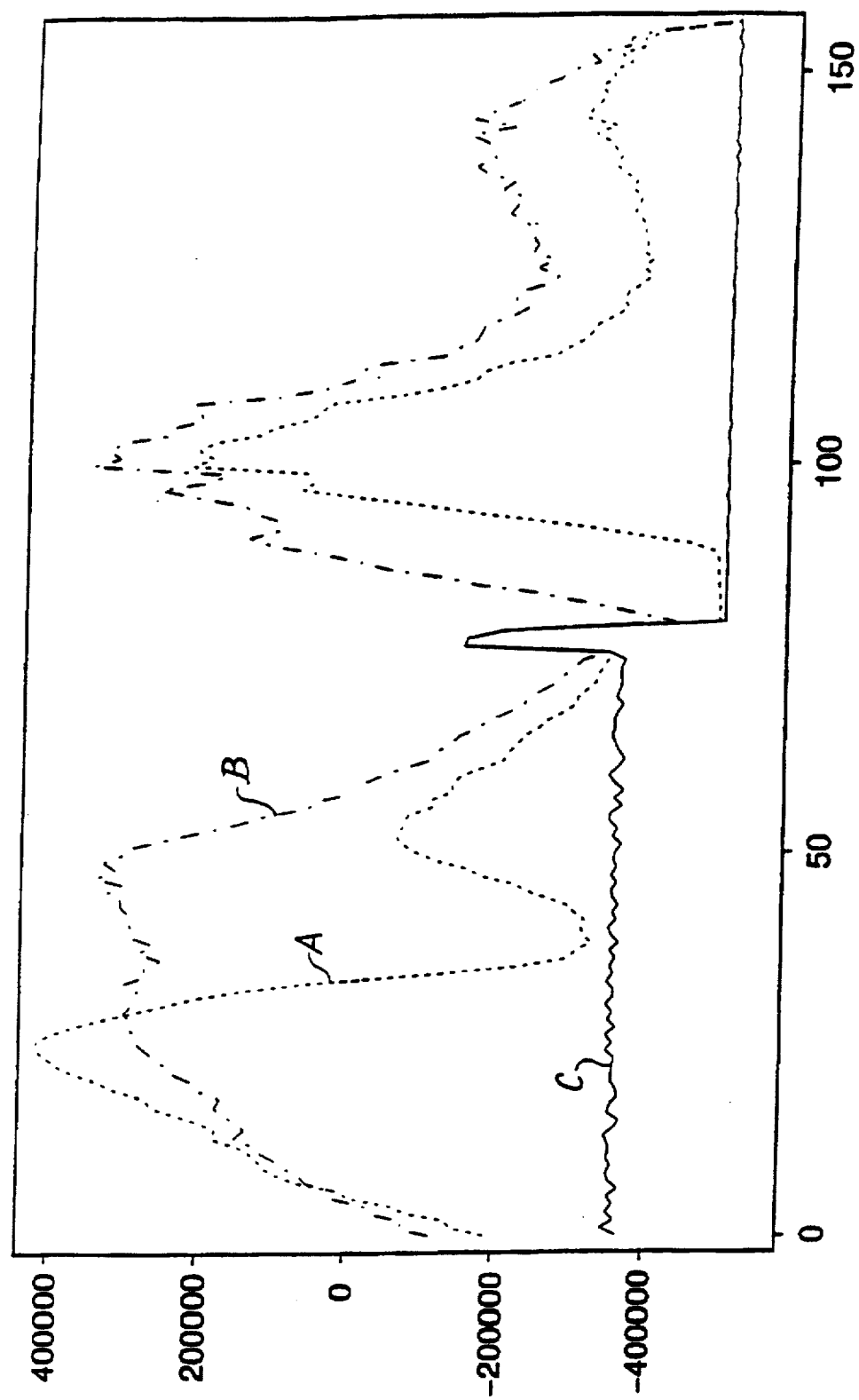

In FIG. 9, the number of counts generated by a specific light detecting element of a specific pixel corresponding to a specific wavelength interval are represented along the ordinate axis. In FIG. 9, three curves A, B and C are shown representing a sample signal, a reference signal and a dark signal, respectively.

Figure 10:
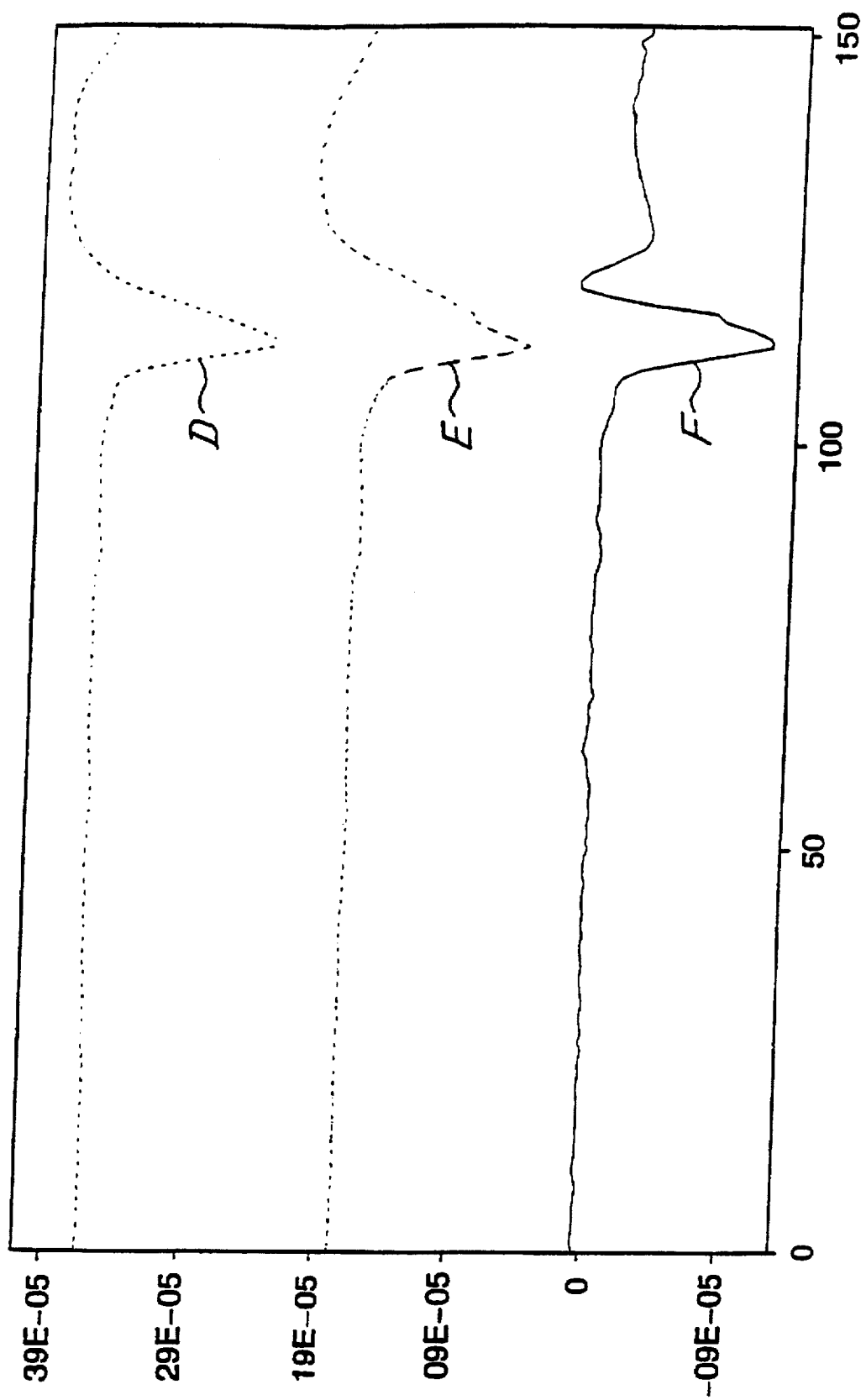
Figure 11:
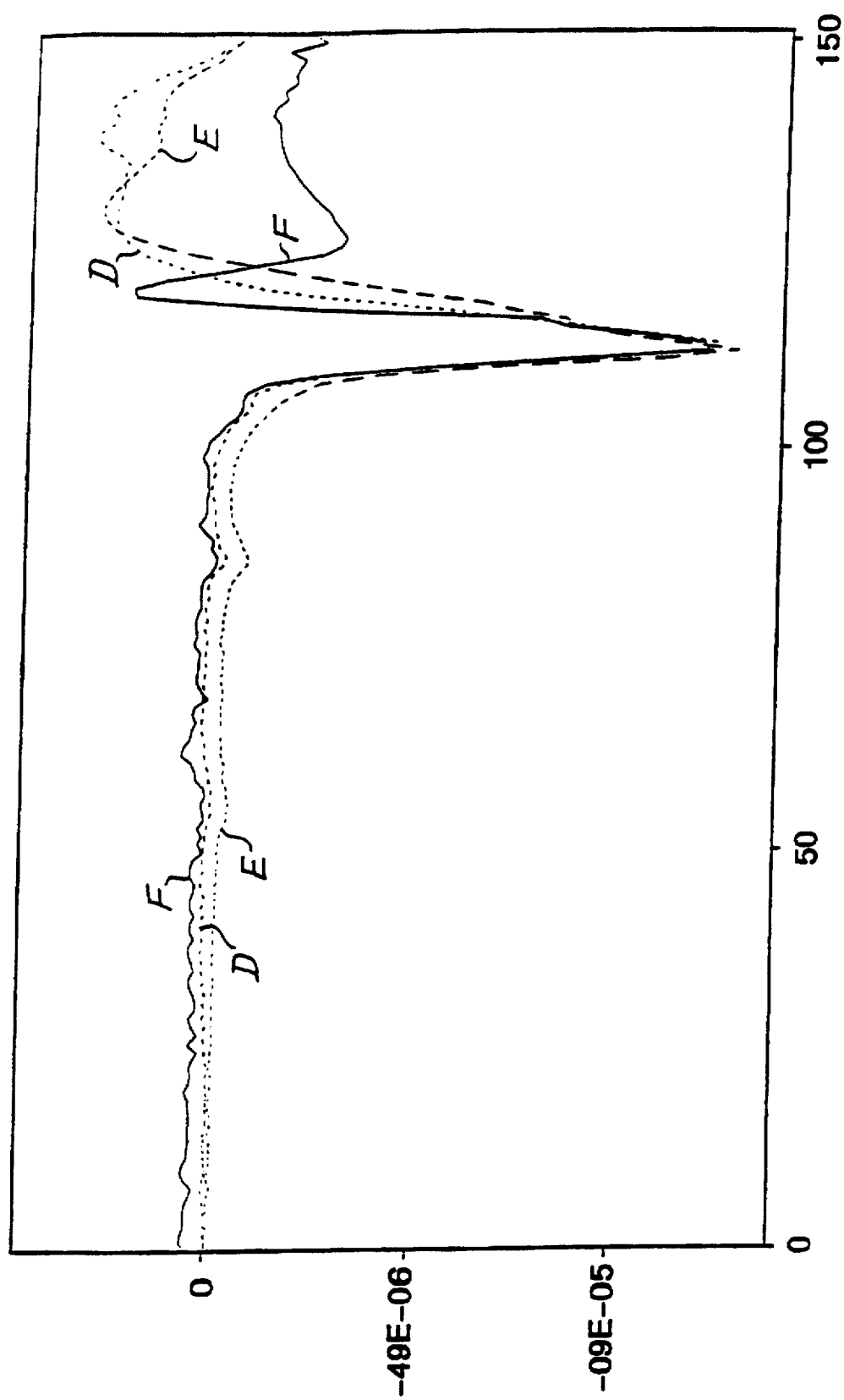

In FIG. 10, three curves D, E and F are shown representing the absorbance of glucose, lactate, and urea, respectively, indicated along the ordinate axis. For clarity curve D and E are shown offset from curve F. From FIG. 10, it in evident that the peak of pixel no. 120 corresponding to the wavelength of 1490 nm of urea is distinguishable from the spectra of e.g. glucose and lactate. For illustrating the possibility of determining urea from e.g. lactate and glucose, the spectra D, E and F are represented in one and the same diagram shown in FIG. 11.

Figure 12:
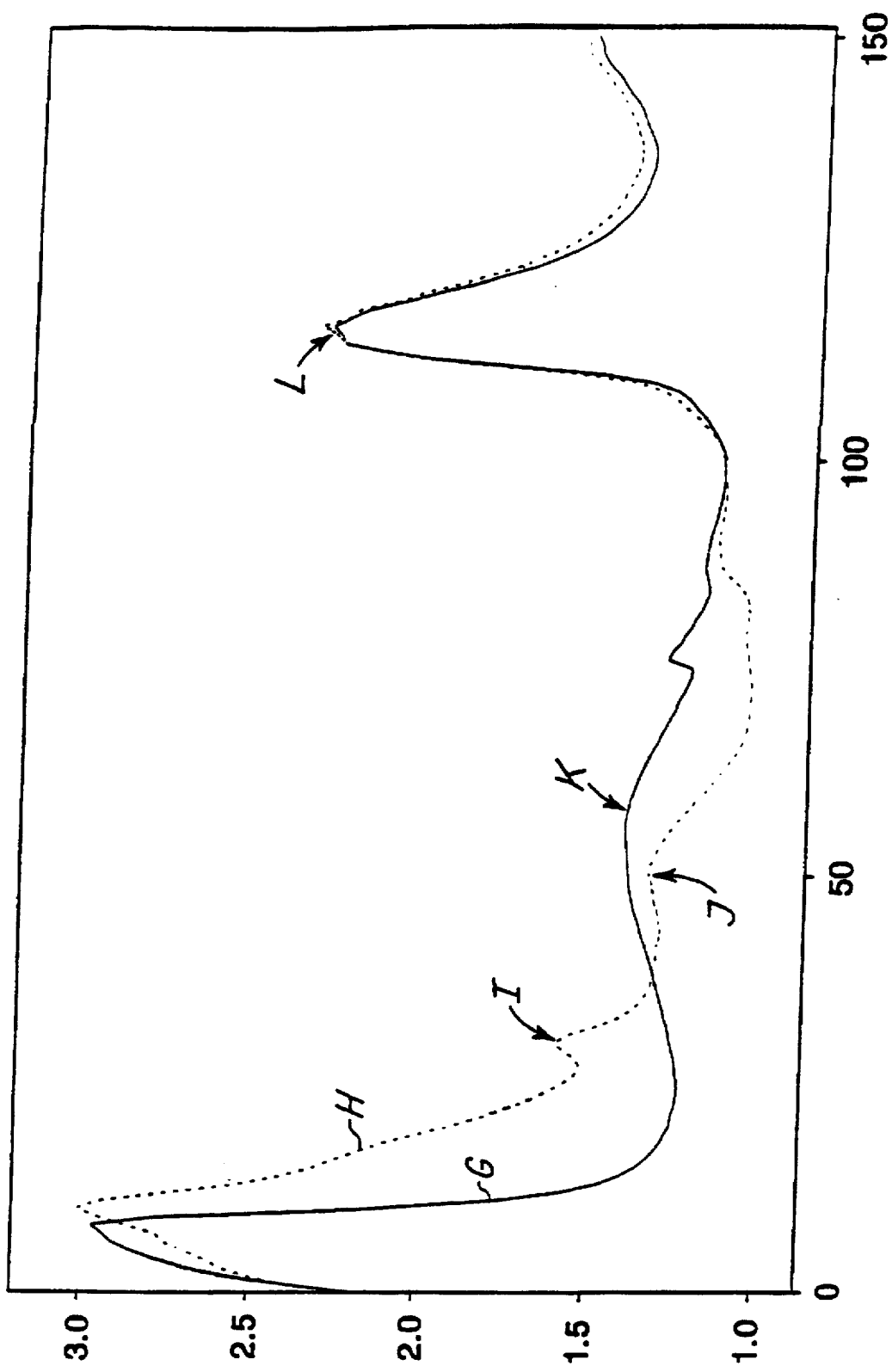

In FIG. 12, two curves G and H are shown representing the absorbance of oxyhemoglobin and deoxyhemoglobin, respectively. In FIG. 12, four references I, J, K, and L are further shown. The references I and J represent peaks characteristics of deoxyhemoglobin and the reference K represents a peak characteristic of oxyhemoglobin. Oxyhemoglobin and deoxyhemoglobin represent 100 and 0 percentage saturated blood, respectively. The reference L indicates a peak characteristic of water. It is to be realized that the peak L in partly overlapping the peaks of the curves D, E, and F shown in FIGS. 10 and 11.

Figure 13:
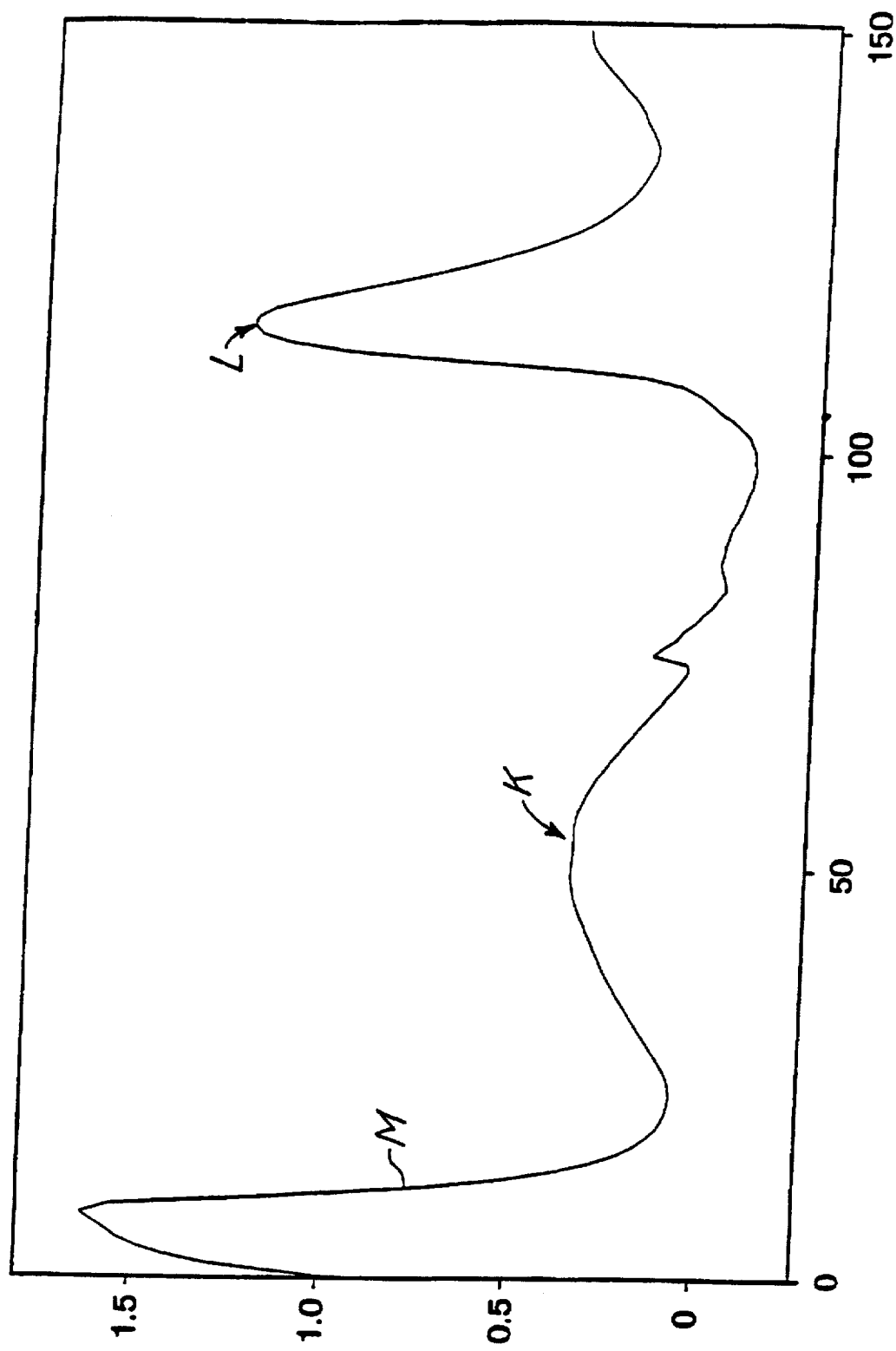

In FIG. 13, a curve M is shown representing the absorbance of a blood sample. The curve M exhibits the characteristic peak K and L of oxyhemoglobin also shown in FIG. 12.

In FIG. 14, the cuvette 24 is shown in greater details. The cuvette 24 in of a symmetrical structure and comprises a central section 286 defining opposite optically transparent plane surfaces together defining a constant flow-through area and an optical transmission path through the blood flowing through the cuvette of the order of 0.5–2.0 mm, preferably 1.0 mm. The cuvette 24 is at opposite ends provided with tubular sections 288 and 290 for establishing connection to external hoses supplying blood to and from the cuvette. Between the tubular sections 288 and 290 and the central section 286 of the cuvette 24, transition sections 289 and 291, respectively, are provided for preventing that the blood flowing from one of the tubular sections 288 and 290 to the central section 286 and vice versa is exposed to excessive pressure or velocity gradients which might deteriorate the blood.

Figure 15:
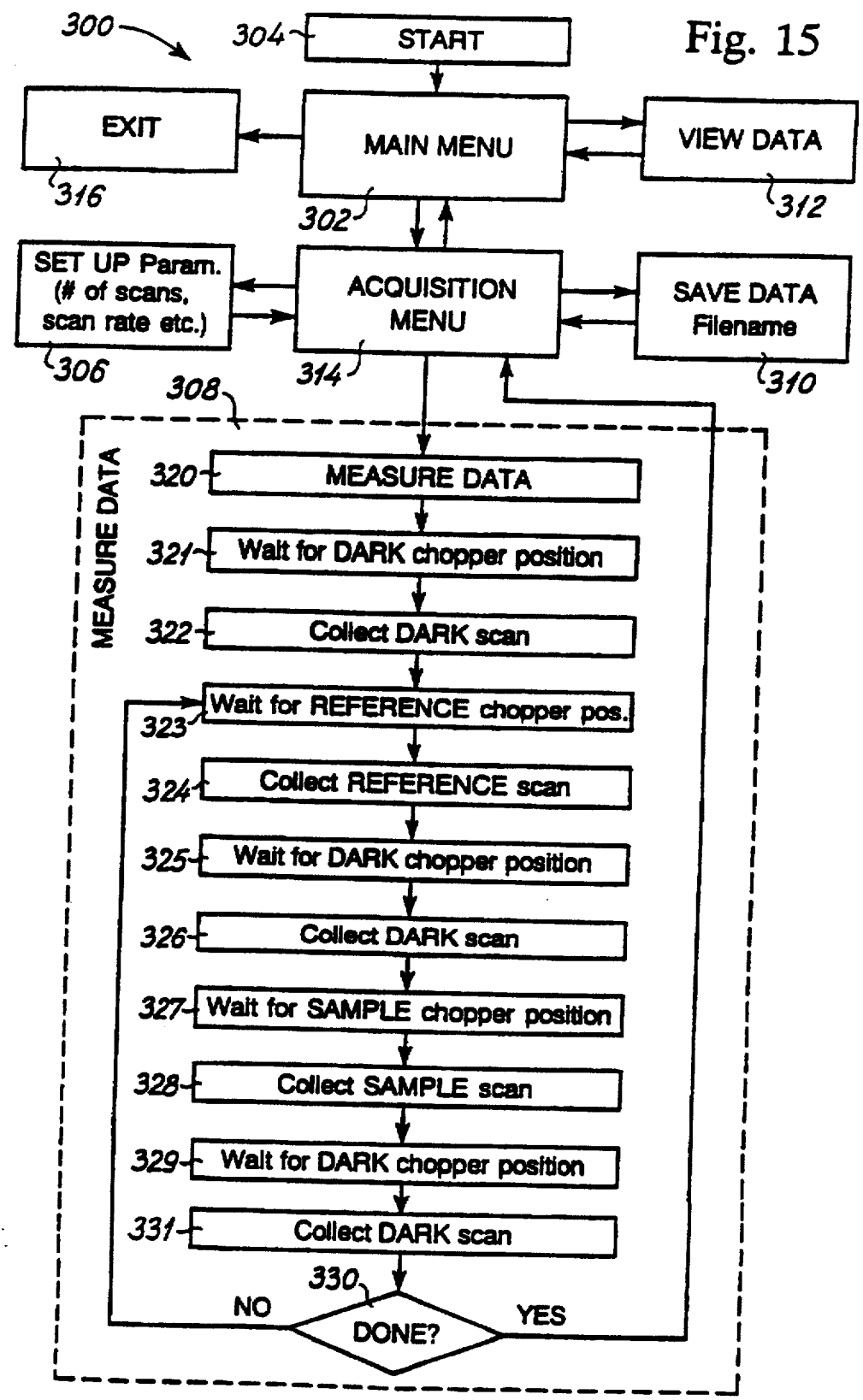
FIG. 15 is a flow chart representation of the software of the personal computer controlling the over-all operation of the whole blood analyzing apparatus shown in FIG. 1.

In FIG. 15, a flow chart of the software of the personal computer is shown, designated the reference numeral 300 in its entirety. The software centrally comprises a "Main menu block" 302 connected to a "Start block" 304, a "View data block" 312 and an "Exit data block" 316. The "Main menu block" 302 is further connected to an "Acquisition menu block" 314 which is further connected to three blocks, a "Set up parameter block" 306, a "Save data block" 310 and a "Measure data block" 308. The "Measure data block" 308 internally comprises a plurality of program steps designated the reference numerals 320–331. The first step is constituted by a "Measure data block" 320, a second step is constituted by a "Wait for dark chopper position block" 321 and a third step is constituted by a "Collect dark scan block" 322. A fifth step is constituted by a "Wait for reference chopper position block" 323, a fourth step is constituted by a "Collect reference scan block" 324, a sixth step is constituted by a "Wait for dark chopper position block" 325, a seventh step is constituted by a "Collect dark scan block" 325, an eigth step is constituted by a "Wait for sample chopper position block" 327, a nineth step in constituted by a "Collect sample scan block" 328, a tenth step is constituted by a "Wait for dark chopper position block" 329, an eleventh step is constituted by a "Collect dark scan block" 331, and a twelfth step is constituted by a "Decision block done? block" 330. Provided the preset number of scans has not been reached, the program reverts to the fourth measuring step of the "Wait for reference chopper position block" 323. Provided the preset number of scans has been reached, the program proceeds to the data "Aquisition menu block" 314.

The data aquisition takes place as follows:

The apparatus provides two channels, each supporting a photodiode detector array constututed by the first and second optical detectors 236 and 242, respectively, of 76 pixels and 4 additional auxiliary inputs. The silicon and germanium diode arrays cover the visible and near infrared regions of the spectrum from 520 to 1800 nanometers.

For maximum noise suppression, data is collected in time intervals based on multiples of power line cycles. Pixels are scanned as to permit the summing of up to eight values of each pixel evenly spaced over the line cycle to enable the contributions of the line frequency to cancel. The user is given complete control over the scan sequence via the Scan-Order table editor.

Acquired data is currently displayed from memory as tables of numerical values. This information may be written to disk for example in the form of ASCII files which may be read into various spread-sheet or spectral interpretation software packages.

REFERENCES

Ref. 1: Haaland, D. M.; Thomas, E. V. Partial least-square methods for spectral analyses. 1. relation to other quantitative calibration methods and the extraction of quantitative information Anal Chem 60:1193–1202 (1988)

Ref. 2: Haaland, D. M.; Thomas, E. V. Partial least-square methods for spectral analyses. 2. Application to simulated and glass spectral data Anal Chem 60:1202–1208 (1988)

Ref. 3: Geladi, P.; Kowalski, B. R. Parial least-square: a tutorial Analytical Chimica Acta 185:1–17 (1986)

Ref. 4: Webster, John G. Encyclopedia of Medical Devices and Instrumentation, Vol. 3: 1695–1711 (1988)

LIST OF REFERENCE NUMERALS

10 Dialysis apparatus
12 Forearm of patient
14 Cannula
16 Hose
18 Arterial pressure monitor
20 Hose
21 Hose loop
22 Hose
24 Cuvette
26 Hose
28 Dialysis fluid inlet hose
30 Dialysis fluid outlet hose
32 Hose
34 Air and foam detector
36 Hose
38 Cannula
40 Dialysis machine
41 Dialysis fluid compartment
42 Blood through-flow compartment
43 Dialysis fluid compartment
44 Blood through-flow compartment
45 Dialysis fluid compartment
50 Hose pump
51 Motor
52 Housing
53 Shaft
54 Roller support body
56 Roller
58 Roller
59 Stem body
60 Switch
61 Electrical signal line
62 Switch
63 Electrical signal line
64 PLL synchronizing circuit block
66 Integrated circuit
68 Integrated circuit
70 Resistor
72 Diode
74 Resistor
76 Diode
78 Operational amplifier
80 Variable resistor
82 Optical fibre or wire
84 Optical fibre or wire
86 Pulse detector
88 Clamping device
90 Hose section
92 Optical detector
94 Optical fibre
96 Optical fibre
98 Power supply
100 Beam-splitting chopper section
101 Supporting plate of beam-splitting chopper section
102 Lamp
103 Optical housing
104 Mirror
106 Mirror
108 Lens
109 First light beam
110 Lens
112 Mirror
113 Second light beam
114 Filter
115 Filter support
116 Filter
117 Filter support
118 Lens
120 Lens
121 Bracket
122 Chopper disc
123 Bracket
124 Protruding rim part
126 Protruding rim part
128 Circumferential recess
130 Circumferential recess
132 Slit
134 Reflecting surface area
136 Motor assembly
137 Gear assembly
138 Output shaft
140 Detector
141 LED
142 Photo-transistor
143 Detector
144 LED
145 Photo-transistor
146 Detector
147 LED
148 Photo-transistor
150 Detector circuit block
151 PCB of detector circuit block
152 LED
154 LED
156 Resistor
158 Resistor
160 Resistor
162 Resistor
164 Resistor
166 Variable resistor 168 Integrated circuit
170 Operational amplifier
172 Variable resistor
174 LED
176 Resistor
180 NPN transistor
181 Switch
182 Resistor
183 Switch
184 Resistor
185 Switch
186 Resistor
187 Switch
188 Resistor
190 Variable resistor
191 Variable resistor
192 Variable resistor
193 Resistor
194 Resistor
195 Resistor
196 Operational amplifier
198 Resistor
200 NPN transistor
202 Resistor
204 Resistor
206 Resistor
208 NPN transistor
210 Capacitor
212 NPN transistor
214 Coil
215 Switch
216 Capacitor
218 Diode
220 Optical fibre
221 Optical fibre fitting
222 Optical fibre
223 Optical fibre fitting
224 Fitting
225 Clamping device
226 Fitting
228 Optical fibre
229 Optical fibre connector
230 Convace holographic grating
232 Beam-splitting mirror
234 Lens
236 First optical detector
238 First optical detector circuit block
239 PCB of first optical detector circuit block
240 Lens
242 Second optical detector
244 Second optical detector circuit block
245 PCB of second optical detector circuit block
246 A/D converter
247 Multicore cable
248 Multipin socket
250 Thermostatically controlled support block
251 Bracket
252 Thermostatical controller
254 Power supply
260 CPU of PC
262 Display of CRT monitor
264 Keyboard
266 Printer
268 Pre-amp
270 Pre-amp
272 Multiplexer
274 Programmable gain and offset block
276 Digital control block
278 Pre-amp
280 Pre-amp
282 Multiplexer
284 Programmable gain and offset block
286 Central section of cuvette 24
288 Tubular section
290 Tubular section
289 Transition section
291 Transition section
300 Software flow chart
302 Main menu block
304 Start block
306 Set up parameter block
308 Measure data block
310 Safe data block
312 View data block
314 Acquisition menu block
316 Exit block
320 Measure data block
321 Wait for dark chopper position block
322 Collect dark scan block
323 Wait for reference chopper position block
324 Collect reference scan block
325 Wait for dark chopper position block
326 Collect dark scan block
327 Wait for sample chopper position block
328 Collect sample scan block
329 Wait for dark chopper position block
330 Decision or done? block
331 Collect dark scan block

We claim:

1. A method of determining the content of a constituent of blood of an individual, comprising:

extracting a whole blood stream of the order of 50–1,000 ml/min from a blood vessel of said individual, directing said whole blood stream through a flow path defining a substantially non-varying flow-through area and comprising a flow-through measuring cuvette constituting part of said flow path, said flow-through measuring cuvette including opposite first and second optically transparent surface parts defining an optical transmission path of the order of 0.5–2.0 mm, propelling said whole blood stream through said flow path by means of a pump causing said whole blood stream to flow through said flow path in a pulsed mode, monitoring said flow of said whole blood stream through said flow-through measuring cuvette of said flow path, so as to determine periods of substantially constant flow of said whole blood stream through said flow-through measuring cuvette, irradiating said first optically transparent surface part of said flow-through measuring cuvette with multi-wavelength near infrared light so as to expose said whole blood stream flowing through said flow-through measuring cuvette to said multi-wavelength near infrared light, detecting the near infrared absorption spectrum represented by near infrared absorption data of said whole blood stream flowing through said flow-through measuring cuvette, and quantifying said content of said constituent by inputting said near infrared absorption data into a mathematical model representing the relation between the near infrared absorption data and the content of said constituent.

2. The method according to claim 1, said non-varying flow-through area being of the order of 5–20 mm$^2$.

3. The method according to claim 1, said flow-through measuring cuvette comprising a central section including said opposite first and second optically transparent surface parts, tubular inlet and outlet sections and first and second transition sections, said first and second transition sections constituting sections connecting said inlet and outlet sections, respectively, to said central section and presenting gradually changing sectional shapes generating to no substantial extent pressure or velocity gradients to said whole blood stream flowing through said flow-through cuvette so as to eliminate to any substantial extent any blood degradating pressure or velocity impact to said blood flow.

4. The method according to claim 1, said mathematical model being established on the basis of a training set of samples-having relevant known variations in composition and thus producing relevant absorption spectra.

5. The method according to claim 4, said quantifying of said content of said constituent further comprising any of the following mathematical analysis techniques: multivariate data analysis technique, e.g. PLS analysis technique (Partial Least Square), PCR analysis technique (Principal Components Regression), MLR analysis technique (Multiple Linear Regression) or artificial neural network analysis technique.

6. A method of determining the content of a constituent of blood of an individual, comprising:
   extracting a whole blood stream of said individual from a blood vessel of said individual,
   directing said whole blood stream through a flow path comprising a flow-through measuring cuvette constituting part of said flow path, said flow-through measuring cuvette including at least one, optically transparent surface part,
   propelling said whole blood stream through said flow path by means of a pump causing said whole blood stream to flow through said flow path in a pulsed mode,
   monitoring said flow of said whole blood stream through said flow-through measuring cuvette of said flow path, so as to determine periods of substantially constant flow of said whole blood stream through said flow-through measuring cuvette,
   irradiating said at least one optically transparent surface part of said flow-through measuring cuvette with electromagnetic radiation of a specific spectral composition, so as to expose said whole blood stream flowing through said flow-through measuring cuvette to said electromagnetic radiation,
   detecting the electromagnetic radiation absorption spectrum, represented by electromagnetic radiation absorption data, of said whole blood stream flowing through said flow-through measuring cuvette at said periods of substantially constant flow of said whole blood stream flowing through said flow-through measuring cuvette, and
   quantifying said content of said constituent by inputting said electromagnetic radiation absorption data into a mathematical model representing the relation between electromagnetic radiation absorption data and the content of said constituent.

7. The method according to claim 6, said flow-through measuring cuvette comprising opposite first and second optically transparent surface parts and defining a substantially non-varying optical transmission path, and said detection of said electromagnetic radiation absorption spectrum being determined by detecting the transmission of said electromagnetic radiation through said whole blood stream flowing through said flow-through measuring cuvette through said optical transmission path thereof.

8. An apparatus for determining the content of a constituent of blood of an individual, comprising:
   means for extracting a whole blood stream from a blood vessel of said individual,
   a flow path defining a substantially non-varying flow-through area,
   means for directing said whole blood stream through said flow path,
   a flow-through measuring cuvette constituting a part of said flow path, said flow-through measuring cuvette including opposite first and second optically transparent surface parts defining an optical transmission path of the order of 0.5–2.0 mm,
   pump means for propelling said whole blood stream through said flow path causing said whole blood stream to flow through said flow path in a pulsed mode,
   means for monitoring said flow of said whole blood stream through said flow-through measuring cuvette of said flow path, so as to determine periods of substantially constant flow of said whole blood stream flowing through said flow-through measuring cuvette,
   means for generating and irradiating said first optically transparent surface part of said flow-through measuring cuvette with multi-wavelength near infrared light so as to expose said whole blood stream flowing through said flow-through measuring cuvette to said multi-wavelength near infrared light,
   detector means for detecting the near infrared absorption spectrum of said whole blood stream flowing through said flow-through measuring cuvette represented by near infrared absorption data, and
   quantifying means for quantifying said content of said constituent by inputting said near infrared absorption data into a mathematical model representing the relation between near infrared absorption data and the content of said constituent.

9. The apparatus according to claim 8, said non-varying flow-through area being of the order of 5–20 $mm^2$.

10. The apparatus according to claim 8, said flow-through measuring cuvette comprising a central section including said opposite first and second optically transparent surface parts, tubular inlet and outlet sections and first and second transition sections, said first and second transition sections constituting sections connecting said inlet and outlet sections, respectively, to said central section and presenting gradually changing sectional shapes generating to no substantial extent pressure or velocity gradients to said whole blood stream flowing through said flow-through cuvette so as to eliminate to any substantial extent any blood degradating pressure or velocity impact to said blood flow.

11. The apparatus according to claim 8, said mathematical model being established on the basis of a training set of samples having relevant known variations in composition and thus producing relevant absorption spectra.

12. The apparatus according to claim 11, said quantifying of said content of said constituent further comprising any of the following mathematical analysis techniques: multivariate data analysis technique, e.g. PLS analysis technique (Partial Least Square), PCR analysis technique (Principal Components Regression), MLR analysis technique (Multiple Linear Regression) or artificial neural network analysis technique.

13. An apparatus for determining the content of a constituent of blood of an individual, comprising:
   means for extracting a whole blood stream of said individual from a blood vessel of said individual, a flow path, means for directing said whole blood stream through said flow path, a flow-through measuring cuvette constituting part of said flow path, said flow-through measuring cuvette including at least one optically transparent surface part, means for propelling said whole blood stream through said flow path, causing said flow-path to flow through said flow path in a pulsed mode, monitor means for monitoring said flow of said whole blood stream through said flow-through measuring cuvette of said flow path, so as to determine periods of substantially constant flow of said whole blood stream flowing through said flow-through measuring cuvette, means for generating and irradiating said at least one optically transparent surface part of said flow-through measuring cuvette with electromagnetic radiation of a specific spectral composition, so as to expose said whole blood stream flowing through said flow-through measuring cuvette to said electromagnetic radiation of said specific spectral composition, detector means for detecting the electromagnetic radiation absorption spectrum, represented by electromagnetic radiation absorption data, of said whole blood stream flowing through said flow-through measuring cuvette at said periods of substantially constant flow of said whole blood stream flowing through said flow-through measuring cuvette, and quantifying means for quantifying said content of said constituent by inputting said electromagnetic radiation absorption data into a mathematical model representing the relation between electromagnetic radiation absorption data and the content of said constituent.

14. The apparatus according to claim 13, said mathematical model being established on the basis of a training set of samples having relevant known variations in composition and thus producing relevant absorption spectra.

15. The apparatus according to claim 14, said quantifying of said content of said constituent further comprising any of the following mathematical analysis techniques: multivariate data analysis technique, e.g. PLS analysis technique (Partial Least Square), PCR analysis technique (Principal Components Regression), MLR analysis technique (Multiple Linear Regression) or artificial neural network analysis technique.

16. A method of hemodialysis treatment, comprising:

extracting a whole blood stream of the order of 50–1,000 ml/min from a blood vessel of an individual, directing said whole blood stream through an extracorporeal flow path to a hemodialyser through a flow path comprising a flow-through measuring cuvette constituting part of said flow path, said flow-through measuring cuvette including opposite first and second optically transparent surface parts defining an optical transmission path of the order of 0.5–2.0 mm, propelling said whole blood stream through said flow path by means of a pump causing said whole blood stream to flow through said flow path in a pulsed mode, monitoring said flow of said whole blood stream through said flow-through measuring cuvette of said flow path, so as to determine periods of substantially constant flow of said whole blood stream through said flow-through measuring cuvette, irradiating said first optically transparent surface part of said flow-through measuring cuvette with multi-wavelength near infrared light comprising light of the wavelength range 700–1,800 nm so as to expose said whole blood stream flowing through said flow-through measuring cuvette to said multi-wavelength near infrared light, detecting the near infrared absorption spectrum of said whole blood stream flowing through said flow-through measuring cuvette represented by near infrared absorption data, quantifying the content of urea of said whole blood stream by inputting said near infrared absorption data into a mathematical model representing the relation between near infrared absorption data and the content of urea.

17. The method according to claim 16, said flow path defining a substantially non-varying flow-through area.

18. The method according to claim 17, said non-varying flow-through area being of the order of 5–20 mm$^2$.

19. The method according to claim 16, further comprising continuing said hemodialysis treatment until the content of urea of said whole blood stream has decreased below a specific threshold.

20. The method according to claim 19, said flow-through measuring cuvette comprising a central section including said opposite first and second optically transparent surface parts, tubular inlet and outlet sections and first and second transition sections, said first and second transition sections constituting sections connecting said inlet and outlet sections, respectively, to said central section and presenting gradually changing sectional shapes generating to no substantial extent pressure or velocity gradients to said whole blood stream flowing through said flow-through cuvette so as to eliminate to any substantial extent any blood degradating pressure or velocity impact to said blood flow.

21. The method according to claim 19, said mathematical model being established on the basis of a training set of samples having relevant known variations in composition and thus producing relevant absorption spectra.

22. The method according to claim 21, said quantifying of said content of said constituent further comprising any of the following mathematical analysis techniques: multivariate data analysis technique, e.g. PLS analysis technique (Partial least Square), PCR analysis technique (Principal Components Regression), MLR analysis technique (Multiple Linear Regression) or artificial neural network analysis technique.

* * * * *